(12) United States Patent
Fallin et al.

(10) Patent No.: US 11,304,705 B2
(45) Date of Patent: Apr. 19, 2022

(54) INDEXED TRI-PLANAR OSTEOTOMY GUIDE AND METHOD

(71) Applicant: CROSSROADS EXTREMITY SYSTEMS, LLC, Memphis, TN (US)

(72) Inventors: T. Wade Fallin, Hyde Park, UT (US); Daniel J. Triplett, Providence, UT (US); Robert W. Hoy, Essex Junction, VT (US)

(73) Assignee: CrossRoads Extremity Systems, LLC, Memphis, TN (US)

( * ) Notice: Subject to any disclaimer, the term of this patent is extended or adjusted under 35 U.S.C. 154(b) by 142 days.

(21) Appl. No.: 16/534,857

(22) Filed: Aug. 7, 2019

(65) Prior Publication Data
US 2019/0357919 A1    Nov. 28, 2019

Related U.S. Application Data

(63) Continuation of application No. 15/047,666, filed on Feb. 19, 2016, now Pat. No. 10,376,268.

(60) Provisional application No. 62/118,378, filed on Feb. 19, 2015.

(51) Int. Cl.
*A61B 17/15* (2006.01)
*A61B 17/14* (2006.01)

(52) U.S. Cl.
CPC ............ *A61B 17/151* (2013.01); *A61B 17/14* (2013.01)

(58) Field of Classification Search
CPC ..... A61B 17/15; A61B 17/151; A61B 17/152; A61B 2017/564; A61B 2017/567; A61B 2017/568
See application file for complete search history.

(56) References Cited

U.S. PATENT DOCUMENTS

| | | |
|---|---|---|
| 4,069,824 A | 1/1978 | Weinstock |
| 4,335,715 A | 6/1982 | Kirkley |
| 4,349,018 A | 9/1982 | Chambers |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,627,425 A | 12/1986 | Reese |
| 4,632,102 A | 12/1986 | Comparetto |
| 4,664,102 A | 5/1987 | Comparetto |
| 4,708,133 A | 11/1987 | Comparetto |

(Continued)

FOREIGN PATENT DOCUMENTS

| | | |
|---|---|---|
| EP | 0 570 187 B1 | 7/1996 |
| WO | WO 00/006036 | 2/2000 |

(Continued)

OTHER PUBLICATIONS

Arthrex Hallux Valgus Solutions, Arthrex, Inc., www.arthrex.com 2009, 2 pp.

(Continued)

*Primary Examiner* — Anu Ramana
(74) *Attorney, Agent, or Firm* — Knobbe, Martens, Olson & Bear, LLP

(57) ABSTRACT

Methods and devices for performing an osteotomy produce a bone cut producing a multi-planar change in the alignment of a bone portion by rotating it relative to another bone portion.

18 Claims, 33 Drawing Sheets

(56) References Cited

U.S. PATENT DOCUMENTS

| | | | |
|---|---|---|---|
| 4,736,737 A | 4/1988 | Fargie et al. | |
| 4,750,481 A | 6/1988 | Reese | |
| 4,757,810 A | 7/1988 | Reese | |
| 4,852,558 A | 8/1989 | Outerbridge | |
| 4,913,144 A | 4/1990 | Del Medico | |
| 4,952,214 A | 8/1990 | Comparetto | |
| 4,959,066 A | 9/1990 | Dunn et al. | |
| 5,035,698 A | 7/1991 | Comparetto | |
| 5,042,983 A | 8/1991 | Rayhack | |
| 5,049,149 A | 9/1991 | Schmidt | |
| 5,053,039 A | 10/1991 | Hofmann et al. | |
| 5,078,719 A | 1/1992 | Schreiber | |
| 5,112,334 A | 5/1992 | Alchermes et al. | |
| 5,147,364 A | 9/1992 | Comparetto | |
| 5,176,685 A | 1/1993 | Rayhack | |
| 5,246,444 A | 9/1993 | Schreiber | |
| 5,413,579 A | 5/1995 | Tom Du Toit | |
| 5,449,360 A | 9/1995 | Schreiber | |
| 5,470,335 A | 11/1995 | Du Toit | |
| 5,540,695 A | 7/1996 | Levy | |
| 5,578,038 A | 11/1996 | Slocum | |
| 5,601,565 A | 2/1997 | Huebner | |
| 5,613,969 A | 3/1997 | Jenkins, Jr. | |
| 5,620,448 A | 4/1997 | Puddu | |
| 5,643,270 A | 7/1997 | Combs | |
| 5,667,510 A | 9/1997 | Combs | |
| H1706 H | 1/1998 | Mason | |
| 5,722,978 A | 3/1998 | Jenkins, Jr. | |
| 5,749,875 A | 5/1998 | Paddu | |
| 5,779,709 A | 7/1998 | Harris, Jr. et al. | |
| 5,843,085 A * | 12/1998 | Graser | A61B 17/151 606/87 |
| 5,911,724 A | 6/1999 | Wehrli | |
| 5,980,526 A | 11/1999 | Johnson et al. | |
| 5,984,931 A | 11/1999 | Greenfield | |
| 6,007,535 A | 12/1999 | Rayhack et al. | |
| 6,027,504 A | 2/2000 | McGuire | |
| 6,030,391 A | 2/2000 | Brainard et al. | |
| 6,203,545 B1 | 3/2001 | Stoffella | |
| 6,248,109 B1 | 6/2001 | Stoffella | |
| 6,391,031 B1 * | 5/2002 | Toomey | A61B 17/15 606/82 |
| 6,547,793 B1 | 4/2003 | McGuire | |
| 6,676,662 B1 | 1/2004 | Bagga et al. | |
| 6,755,838 B2 | 6/2004 | Trnka | |
| 6,796,986 B2 | 9/2004 | Duffner | |
| 7,018,383 B2 | 3/2006 | McGuire | |
| 7,112,204 B2 | 9/2006 | Justin et al. | |
| 7,182,766 B1 | 2/2007 | Mogul | |
| 7,540,874 B2 | 6/2009 | Trumble et al. | |
| 7,572,258 B2 * | 8/2009 | Stiernborg | A61B 17/15 606/79 |
| 7,691,108 B2 | 4/2010 | Lavallee | |
| 7,763,026 B2 | 7/2010 | Egger | |
| 7,967,823 B2 | 6/2011 | Novak et al. | |
| 7,972,338 B2 * | 7/2011 | O'Brien | A61B 17/152 606/87 |
| 8,062,301 B2 | 11/2011 | Ammann et al. | |
| 8,083,746 B2 | 12/2011 | Novak | |
| 8,137,406 B2 | 3/2012 | Novak et al. | |
| 8,236,000 B2 | 8/2012 | Novak et al. | |
| 8,262,664 B2 | 9/2012 | Justin | |
| 8,277,459 B2 | 10/2012 | Sand et al. | |
| 8,282,645 B2 * | 10/2012 | Lawrence | A61B 17/15 606/87 |
| 8,313,492 B2 | 11/2012 | Wong | |
| 8,409,209 B2 | 4/2013 | Ammann et al. | |
| 8,496,662 B2 | 7/2013 | Novak et al. | |
| 8,529,571 B2 | 9/2013 | Horan et al. | |
| 8,540,777 B2 | 9/2013 | Ammann et al. | |
| 8,545,508 B2 | 10/2013 | Collazo | |
| D695,402 S | 12/2013 | Dacosta et al. | |
| 8,652,142 B2 | 2/2014 | Geissler | |
| 8,657,820 B2 | 2/2014 | Kubiak et al. | |
| 8,702,715 B2 | 4/2014 | Ammann et al. | |
| 8,771,279 B2 | 7/2014 | Philippon et al. | |
| 8,777,948 B2 | 7/2014 | Bernsteiner | |
| 8,888,785 B2 | 11/2014 | Ammann | |
| 8,900,247 B2 | 12/2014 | Tseng et al. | |
| 8,906,026 B2 | 12/2014 | Ammann et al. | |
| 9,060,822 B2 | 6/2015 | Lewis et al. | |
| 9,113,920 B2 | 8/2015 | Ammann | |
| 9,622,805 B2 | 4/2017 | Santrock | |
| 9,687,250 B2 * | 6/2017 | Dayton | A61B 17/15 |
| 9,814,474 B2 * | 11/2017 | Montoya | A61B 17/151 |
| 9,907,558 B2 | 3/2018 | Fallin et al. | |
| 9,936,994 B2 | 4/2018 | Smith et al. | |
| 10,045,807 B2 | 8/2018 | Santrock et al. | |
| 10,245,086 B2 | 4/2019 | Treace et al. | |
| 10,245,088 B2 | 4/2019 | Dayton et al. | |
| 10,292,713 B2 | 5/2019 | Fallin et al. | |
| 10,335,220 B2 | 7/2019 | Smith et al. | |
| 10,342,590 B2 | 7/2019 | Bays et al. | |
| 10,376,268 B2 | 8/2019 | Fallin et al. | |
| 10,470,779 B2 | 11/2019 | Fallin et al. | |
| 10,512,470 B1 | 12/2019 | Bays et al. | |
| 10,555,757 B2 | 2/2020 | Dayton | |
| 10,561,426 B1 | 2/2020 | Dayton et al. | |
| 10,575,862 B2 | 3/2020 | Bays et al. | |
| 10,743,995 B2 | 8/2020 | Fallin et al. | |
| 10,898,211 B2 | 1/2021 | Fallin et al. | |
| 11,058,546 B2 | 7/2021 | Hollis et al. | |
| 11,116,558 B2 | 9/2021 | Smith et al. | |
| 11,147,590 B2 | 10/2021 | Dayton | |
| 11,160,567 B2 | 11/2021 | Fallin et al. | |
| 2002/0165552 A1 | 11/2002 | Duffner | |
| 2004/0097946 A1 | 5/2004 | Dietzel | |
| 2004/0138669 A1 | 7/2004 | Horn | |
| 2005/0070909 A1 | 3/2005 | Egger | |
| 2005/0149042 A1 | 7/2005 | Metzger | |
| 2005/0228389 A1 * | 10/2005 | Stiernborg | A61B 17/152 606/79 |
| 2005/0251147 A1 | 11/2005 | Novak | |
| 2005/0273112 A1 | 12/2005 | McNamara | |
| 2006/0129163 A1 | 6/2006 | McGuire | |
| 2006/0264961 A1 | 11/2006 | Murray | |
| 2007/0010818 A1 | 1/2007 | Stone | |
| 2007/0265634 A1 * | 11/2007 | Weinstein | A61B 17/15 606/87 |
| 2007/0276383 A1 | 11/2007 | Rayhack | |
| 2008/0015603 A1 | 1/2008 | Collazo | |
| 2008/0039850 A1 | 2/2008 | Rowley | |
| 2008/0147073 A1 | 6/2008 | Ammann | |
| 2008/0195215 A1 | 8/2008 | Morton | |
| 2008/0269908 A1 | 10/2008 | Warburton | |
| 2009/0036931 A1 | 2/2009 | Pech | |
| 2009/0054899 A1 | 2/2009 | Ammann | |
| 2009/0210010 A1 | 8/2009 | Strnad et al. | |
| 2009/0222047 A1 | 9/2009 | Graham | |
| 2010/0125300 A1 | 5/2010 | Blitz et al. | |
| 2010/0130981 A1 | 5/2010 | Richards | |
| 2010/0152782 A1 | 6/2010 | Stone et al. | |
| 2011/0178524 A1 | 7/2011 | Lawrence | |
| 2011/0188550 A1 | 8/2011 | Orbay | |
| 2011/0213376 A1 | 9/2011 | Maxson et al. | |
| 2011/0224734 A1 | 9/2011 | Schelling | |
| 2012/0016426 A1 | 1/2012 | Robinson | |
| 2012/0185056 A1 | 7/2012 | Warburton | |
| 2012/0191199 A1 | 7/2012 | Raemisch | |
| 2012/0303033 A1 | 11/2012 | Weiner et al. | |
| 2013/0012949 A1 | 1/2013 | Fallin | |
| 2013/0090662 A1 | 4/2013 | Hanson et al. | |
| 2013/0172942 A1 | 7/2013 | Lewis et al. | |
| 2013/0226248 A1 | 8/2013 | Hatch | |
| 2013/0226252 A1 | 8/2013 | Mayer | |
| 2013/0331845 A1 | 12/2013 | Horan | |
| 2014/0188139 A1 | 7/2014 | Fallin | |
| 2014/0194999 A1 | 7/2014 | Orbay | |
| 2014/0343555 A1 | 11/2014 | Russi | |
| 2015/0057667 A1 | 2/2015 | Ammann | |
| 2015/0245858 A1 | 9/2015 | Ammann | |
| 2016/0015426 A1 | 1/2016 | Dayton | |
| 2016/0192950 A1 | 7/2016 | Dayton et al. | |

(56) References Cited

U.S. PATENT DOCUMENTS

| | | | |
|---|---|---|---|
| 2016/0192970 A1 | 7/2016 | Dayton et al. | |
| 2016/0235414 A1* | 8/2016 | Hatch | A61B 17/151 |
| 2016/0324532 A1* | 11/2016 | Montoya | A61B 17/1728 |
| 2016/0324555 A1 | 11/2016 | Brumfield et al. | |
| 2016/0354127 A1 | 12/2016 | Lundquist et al. | |
| 2017/0007305 A1 | 1/2017 | Hollis et al. | |
| 2017/0014143 A1 | 1/2017 | Dayton et al. | |
| 2017/0014173 A1 | 1/2017 | Smith et al. | |
| 2017/0042598 A1 | 2/2017 | Santruck et al. | |
| 2017/0042599 A1 | 2/2017 | Bays et al. | |
| 2017/0049576 A1 | 2/2017 | Guilford et al. | |
| 2017/0079669 A1 | 3/2017 | Bays et al. | |
| 2017/0164989 A1 | 6/2017 | Weiner et al. | |
| 2017/0172638 A1 | 6/2017 | Santrock et al. | |
| 2017/0196602 A1 | 7/2017 | Lundquist et al. | |
| 2018/0125504 A1 | 5/2018 | Dayton et al. | |
| 2019/0175238 A1 | 6/2019 | Dayton et al. | |
| 2019/0274745 A1 | 9/2019 | Smith et al. | |
| 2019/0328435 A1 | 10/2019 | Bays et al. | |
| 2019/0328436 A1 | 10/2019 | Bays et al. | |
| 2020/0015856 A1 | 1/2020 | Treace et al. | |
| 2020/0078025 A1 | 3/2020 | Fallin et al. | |
| 2020/0138491 A1 | 5/2020 | Brigido et al. | |
| 2020/0197021 A1 | 6/2020 | Dayton et al. | |
| 2020/0375644 A1 | 12/2020 | Smith et al. | |
| 2021/0026357 A1 | 2/2021 | Hollis et al. | |
| 2021/0077192 A1 | 3/2021 | Perler et al. | |
| 2021/0251670 A1 | 8/2021 | Sayger et al. | |
| 2021/0282823 A1 | 9/2021 | Day et al. | |
| 2021/0307763 A1 | 10/2021 | Fallin et al. | |
| 2021/0338450 A1 | 11/2021 | Hollis et al. | |

FOREIGN PATENT DOCUMENTS

| | | |
|---|---|---|
| WO | WO 04/075775 | 9/2004 |
| WO | WO 04/089227 | 10/2004 |
| WO | WO 05/041785 | 5/2005 |
| WO | WO 07/008348 | 1/2007 |
| WO | WO 08/097781 | 8/2008 |
| WO | WO 16/134154 | 8/2016 |
| WO | WO 16/134160 | 8/2016 |
| WO | WO 17/011589 | 1/2017 |
| WO | WO 17/031000 | 2/2017 |
| WO | WO 17/049056 | 3/2017 |
| WO | WO 21/021640 | 2/2021 |
| WO | WO 21/026357 | 2/2021 |

OTHER PUBLICATIONS

Comprehensive Solutions for Forefoot and Midfood Surgery using the Mini TightRope System, Arthrex, Inc., www.arthrex.com 2012, 15 pp.

Distal Extremities Orthopaedic Update, Arthrex, Inc., www.arthrex.com, 2014, 24 pp.

Dobbe, et al., "Computer-Assisted and Patient-Specific 3-D Planning and Evaluation of a Single-Cut Rotational Osteotomy for Complex Long-Bone Deformities", Med Biol Eng Comput (2011) 49:1363-1370.

Foot & Ankle Repair and Reconstruction Technology, Arthrex GmbH, www.arthrex.com, 2016, 86 pp.

Gregg, Julie, et al., "Plantar Plate Repair and Weil Osteotomy for Meteatarsophalangeal Joint Instability", Foot and Ankle Surgery 13(2007) 116-121.

Meyer, D.C., et al., "A New Methodology for the Planning of Single-Cut Corrective Osteotomies of Mal-Aligned Long Bones", Clinical Biomechanics 20(2005) 223-227.

Oscillating Saw Attachment for EPD/APD, Colibri II and Small Electric Drive, Synthes GmbH, www.synthes.com, 2012, 2 pp.

Scarf Osteotomy Technical Information Sheet, TALUS group of GECO, www.geco-medical.org, 2004, 2 pp.

Shurnas, Paul S., M.D., et al., Proximal Metatarsal Opening Wedge Osteotomy: PMOW—Arthrex LPS System, Arthrex, Inc., www.arthrex.com, 2008, 1 pp.

Speed Triad Medial Technique, BioMedical Enterprises, www.bme-tx.com, 2015, 2 pp.

The Accu-Cut Osteotomy Guide System, BioPro Implants, www.bioproimplants.com, Brochure No. 16932 Rev07, 2 pp.

The Accu-Cut Osteotomy Guide System, BioPro Implants, www.bioproimplants.com. Brochure No. 17136. Rev4, 2 pp.

The Next Generation in Foot & Ankle Repair and Reconstruction Technology, Arthrex, Inc., www.arthrex.com, 2016, 76 pp.

Weil, Lowell Jr., et al., "Anatomic Plantar Plate Repair Using the Weil Metatarsal Osteotomy Approach", Foot & Ankle Specialist, http://fas.sagepub.com/, 2011, 7 pp.

DiDomenico, Lawrence A., et al. "Lapidus Bunionectomy: First Metatarsal-Cuneiform Arthrodesis," Southerland, Chapter 31, Aug. 18, 2012.

* cited by examiner

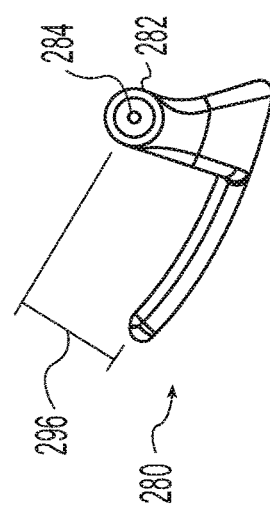
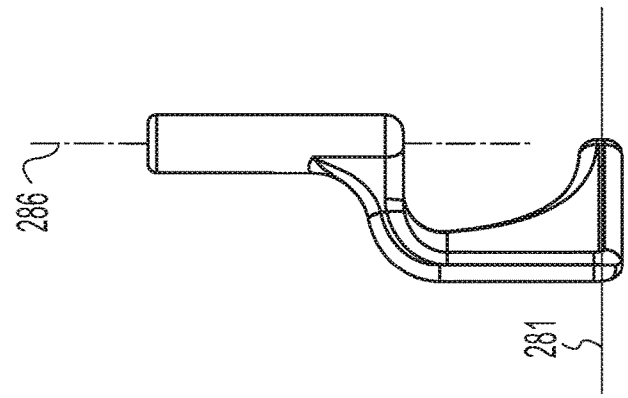
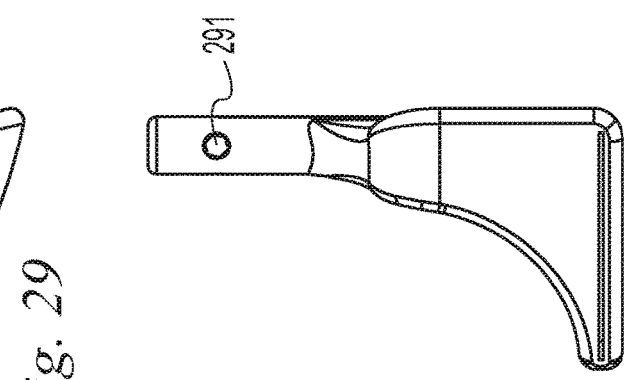
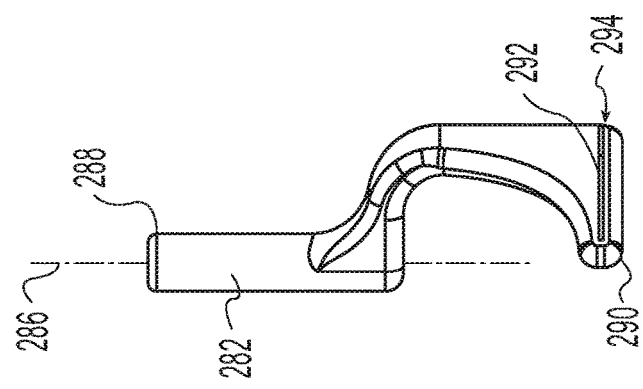
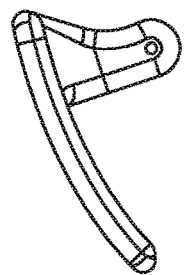

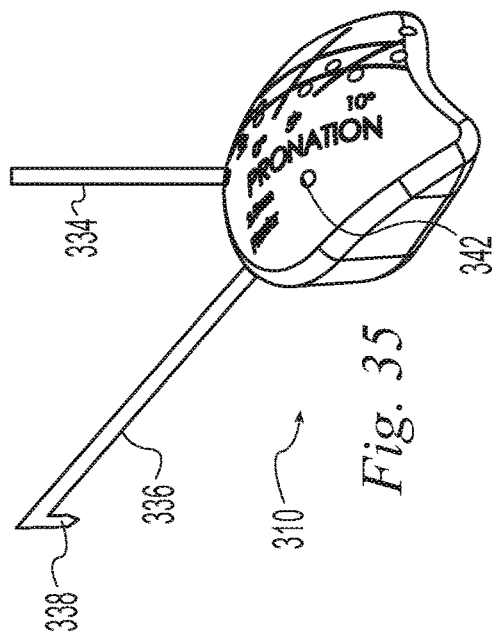
Fig. 35
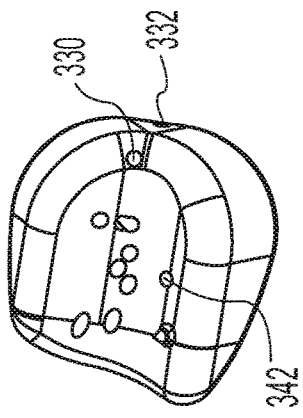
Fig. 40
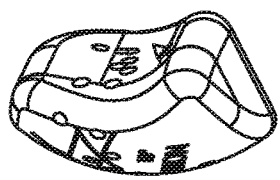
Fig. 39
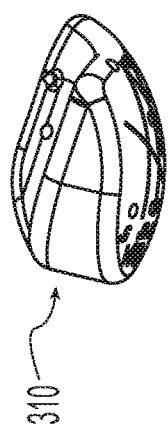
Fig. 36
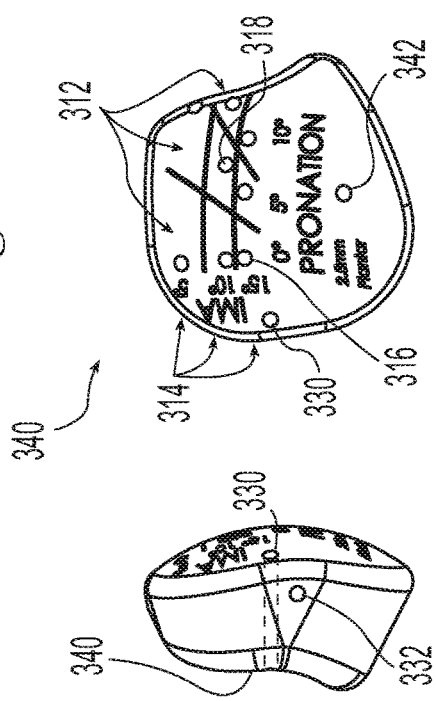
Fig. 38
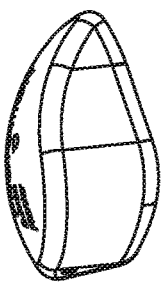
Fig. 41
Fig. 37

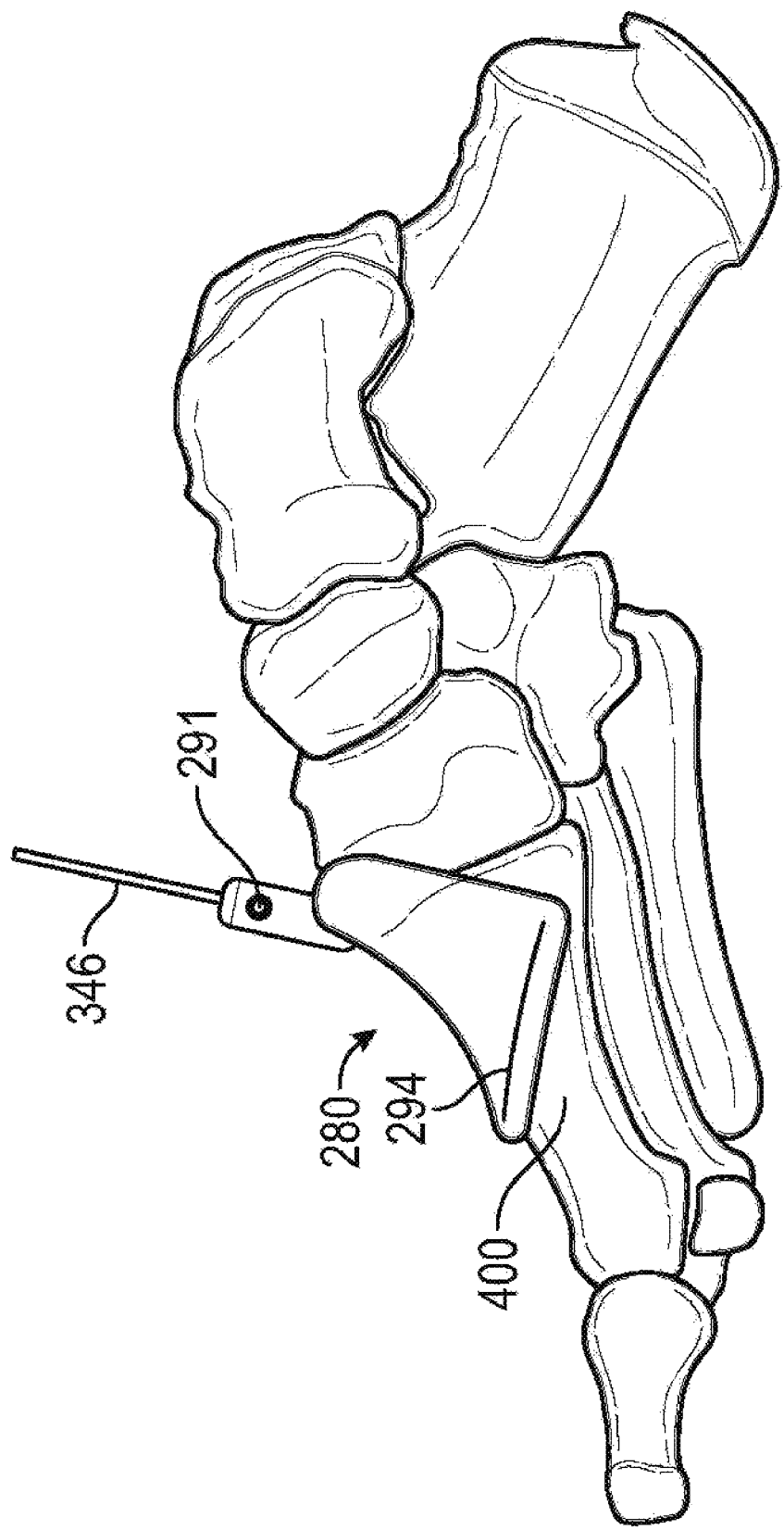

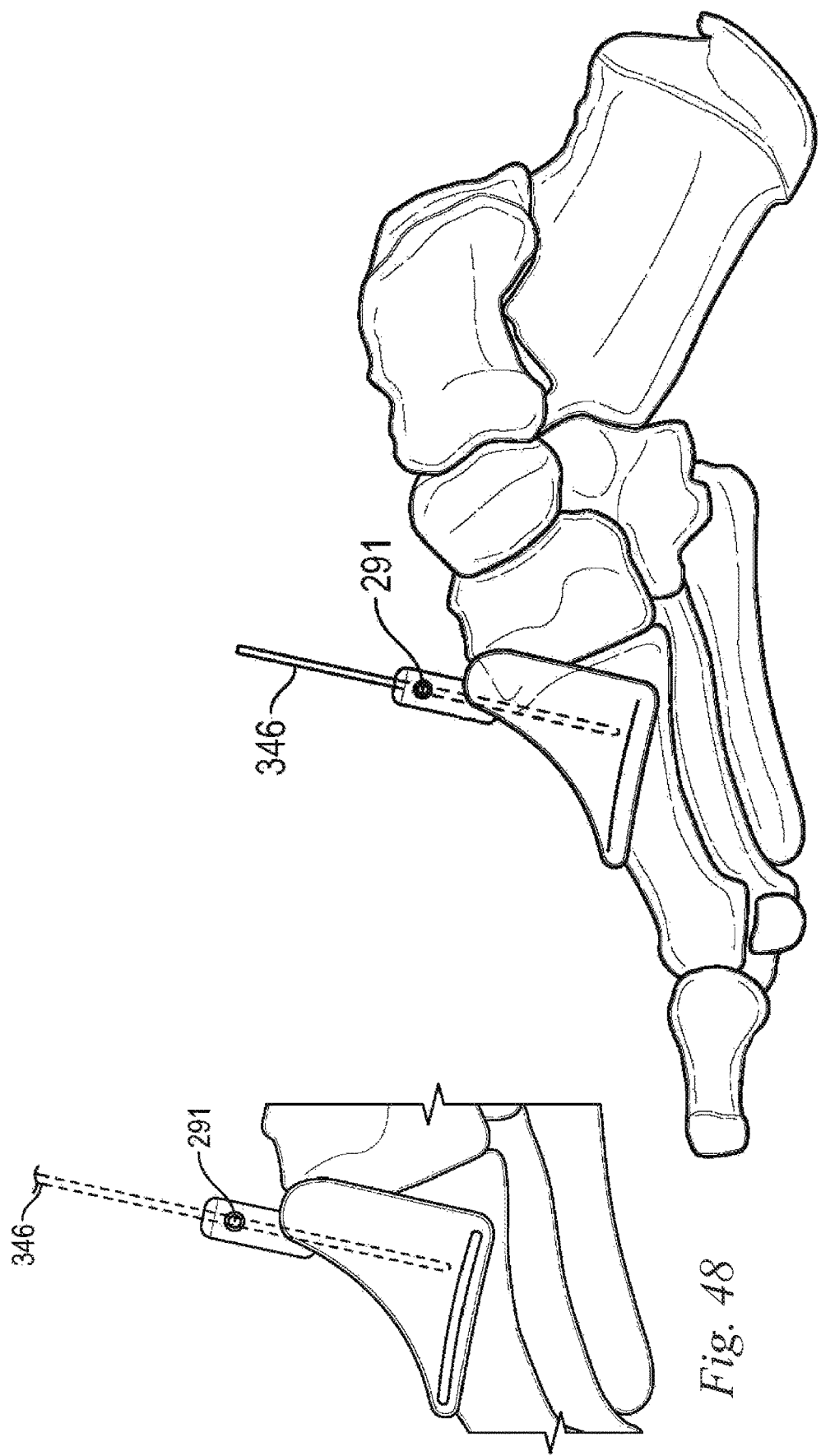

INDEXED TRI-PLANAR OSTEOTOMY GUIDE AND METHOD

CROSS REFERENCE TO RELATED PATENT APPLICATIONS

This application is a continuation of U.S. patent application Ser. No. 15/047,666 filed Feb. 19, 2016, entitled "Indexed Tri-Planar Osteotomy Guide and Method", which claims the benefit of U.S. Provisional Application No. 62/118,378, filed Feb. 19, 2015, entitled "Indexed Tri-Planar Osteotomy Guide and Method". The foregoing is incorporated herein by reference in their entirety.

FIELD OF THE INVENTION

The invention relates to methods, implants, and instruments for performing an osteotomy.

BACKGROUND

Various conditions may affect skeletal joints such as the deterioration, elongation, shortening, or rupture of soft tissues, cartilage, and/or bone associated with the joint and consequent laxity, pain, and/or deformity. It is often desirable to change the angular alignment of a bone or a portion of a bone to restore function and/or reduce pain. To this end, various osteotomy procedures and instruments have been proposed. For example, osteotomies have been performed throughout the body to make various angular adjustments such as in a tibia, fibula, femur, pelvis, humerus, ulna, radius, metacarpal, metatarsal, and other bones.

SUMMARY

The present invention provides methods, implants, and instruments for performing an osteotomy.

In one example of the invention, methods and devices for performing an osteotomy produce a bone cut allowing multi-planar correction of the alignment of a bone portion by rotating it relative to another bone portion.

In another example of the invention, an osteotomy system operable to guide the formation of a tri-planar rotational osteotomy between a proximal portion of a metatarsal bone and a distal portion of the metatarsal bone, includes at least one cutter guide and a cutter. The cutter guide includes reference features operable to align the cutter guide with the metatarsal bone in a predetermined position and one or more cutter guiding features each defining an osteotomy plane or rotation axis relative to the metatarsal bone and corresponding to a coupled change in at least two of intermetatarsal angle, pronation, and plantar flexion of the distal portion of the metatarsal bone, at least one of the change in intermetatarsal angle, pronation, and plantar flexion being user selectable among a plurality of values at the time of surgery. The cutter is operable to selectively reference one of the one or more cutter guiding features to cut the metatarsal bone to mobilize the proximal portion of the metatarsal bone and the distal portion of the metatarsal bone relative to one another and produce cut surfaces on which the distal metatarsal bone portion and proximal metatarsal bone portion are relatively rotatable.

In another example of the invention, a method of performing an osteotomy on a metatarsal bone having a proximal portion and a distal portion, the proximal and distal portions defining a first relative position between them, includes determining a desired positional change between the proximal portion of the metatarsal bone and the distal portion of the metatarsal bone in at least two anatomic reference planes; mounting a guide on the metatarsal bone; establishing an osteotomy plane or rotational axis with the guide; guiding a cutter in the osteotomy plane or about the rotational axis to mobilize the proximal portion of the metatarsal bone and the distal portion of the metatarsal bone relative to one another and produce cut surfaces on which the distal portion of the metatarsal bone and proximal portion of the metatarsal bone are relatively rotatable, the cut surfaces being oriented to incorporate the desired positional change in the at least two anatomic reference planes; rotating the distal portion of the metatarsal bone relative to the proximal portion of the metatarsal bone to a second relative position different from the first relative position; and fixing the distal portion of the metatarsal bone and the proximal portion of the metatarsal bone relative to one another in the second relative position with the cut surfaces of the proximal portion of the metatarsal bone and the distal portion of the metatarsal bone abutting one another.

BRIEF DESCRIPTION OF THE DRAWINGS

Various examples of the present invention will be discussed with reference to the appended drawings. These drawings depict only illustrative examples of the invention and are not to be considered limiting of its scope.

FIGS. 29-34 are orthographic views of a cut guide according to the present invention;

FIG. 35 is an isometric view of an axis guide according to the present invention;

FIGS. 36-41 are orthographic views of the axis guide of FIG. 35;

FIGS. 42-54 illustrate a method of performing an osteotomy on a bone according to the present invention;

DESCRIPTION OF THE ILLUSTRATIVE EXAMPLES

The following illustrative examples describe implants, instruments and techniques for performing an osteotomy. The present invention may be used to perform osteotomies on any bone including but not limited to a tibia, fibula, femur, pelvis, humerus, ulna, radius, metacarpal, and metatarsal.

While instruments and techniques according to the present invention may be used in conjunction with any bone or joint, the illustrative examples are shown in a size and form most suitable for the joints of the hand and foot. The hand and foot have a similar structure. Each has a volar aspect. In the hand the volar, or palmar, aspect includes the palm of the hand and is the gripping side of the hand. In the foot the volar, or plantar, aspect is the sole of the foot and is the ground contacting surface during normal walking. Both the hand and foot have a dorsal aspect opposite the volar aspect. Both the hand and foot include long bones generically described as metapodial bones. In the hand, the metapodial bones are referred to as metacarpal bones. In the foot, the metapodial bones are referred to as metatarsal bones. Both the hand and foot include a plurality of phalanges that are the bones of the digits, i.e. the fingers and toes. In both the hand and foot, each of the most proximal phalanges forms a joint with a corresponding metapodial bone. For convenience, the invention will be illustrated with reference to a metatarsus of the first ray of a human foot.

Figure 1:
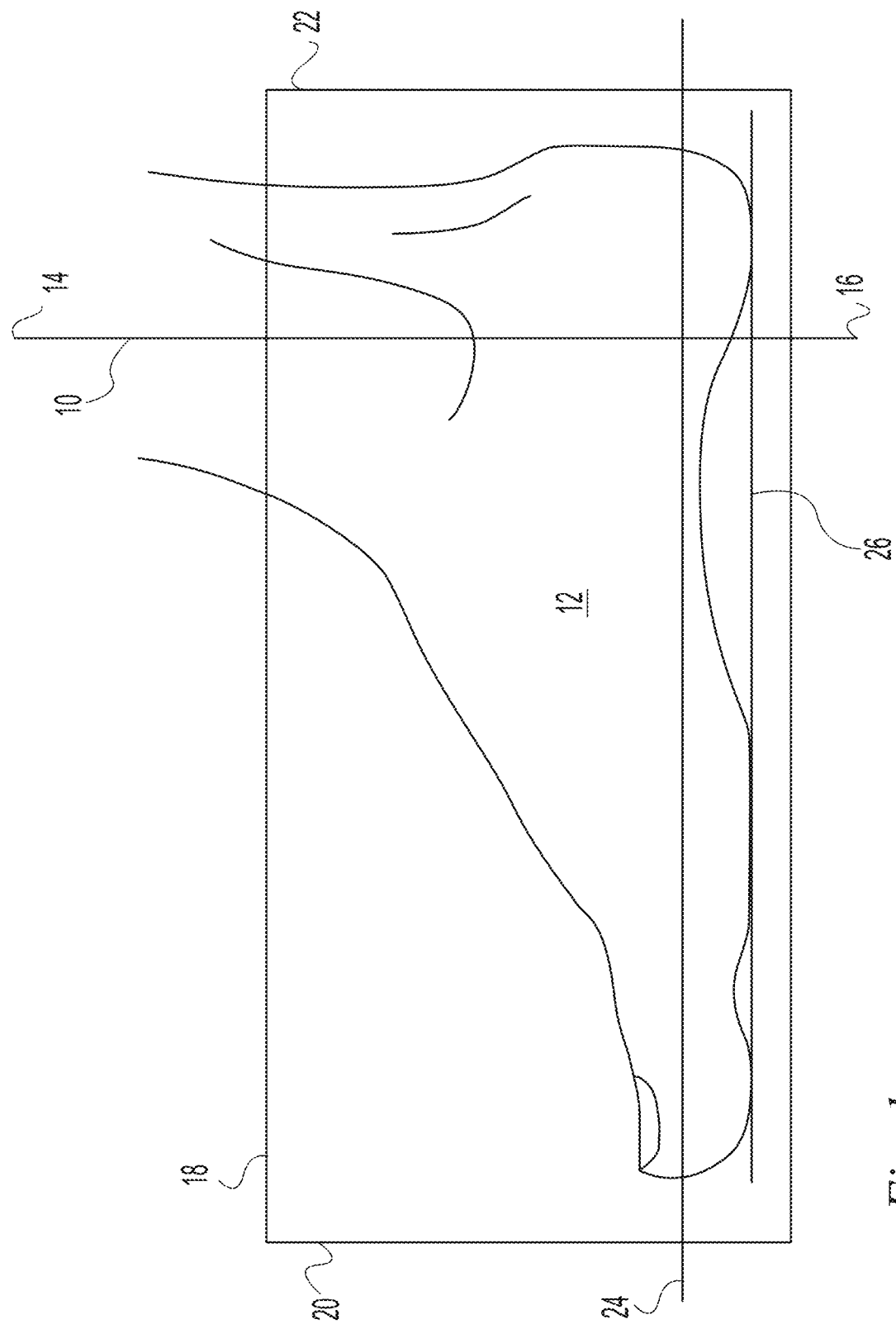
FIG. 1 is medial view of a foot illustrating anatomic reference planes and relative directions.

FIG. 1 illustrates the orientation of anatomic planes and relative directional terms that are used for reference in this application. The coronal plane 10 extends from medial 12 (toward the midline of the body) to lateral (away from the midline of the body) and from dorsal 14 (toward the top of the foot) to plantar 16 (toward the sole of the foot). The sagittal plane 18 extends from anterior 20 (toward the front of the body) to posterior 22 (toward the back of the body) and from dorsal 14 to plantar 16. The transverse plane 24 extends anterior 20 to posterior 22 and medial to lateral parallel to the floor 26. Relative positions are also described as being proximal or distal where proximal is along the lower extremity toward the knee and distal is along the lower extremity toward the toes. The following examples serve to demonstrate the relative directions. The great toe is medial of the lesser toes and the fifth toe is lateral of the great toe. The toes are distal to the heel and the ankle is proximal to the toes. The instep is dorsal and the arch is plantar. The toenails are dorsal and distal on the toes.

Figure 2:
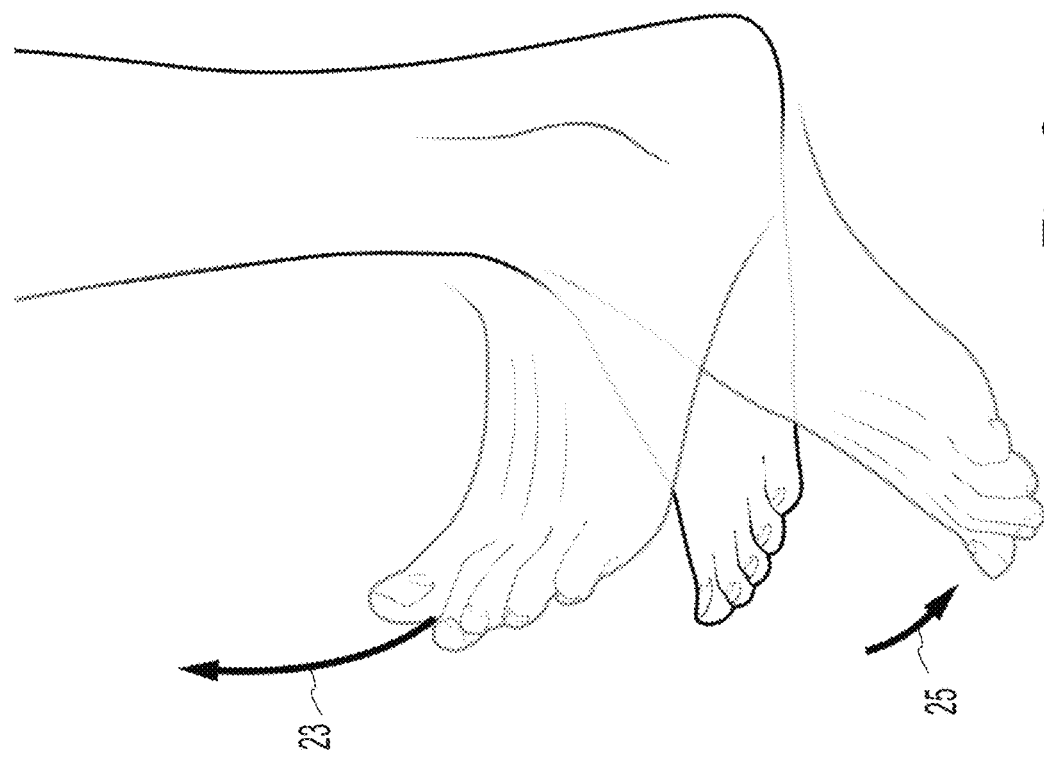
FIG. 2 is a lateral view of a foot illustrating dorsiflexion and plantar flexion.

FIG. 2 illustrates dorsiflexion 23 in which the toes are moved dorsally, or closer to the shin, by decreasing the angle between the dorsum of the foot and the leg and plantar flexion 25 in which the toes are moved plantar, or further away from the shin, by increasing the angle between the dorsum of the foot and the leg. For example when one walks on their heels, the ankle is dorsiflexed and when one walks on their toes, the ankle is plantar flexed.

Figure 3:
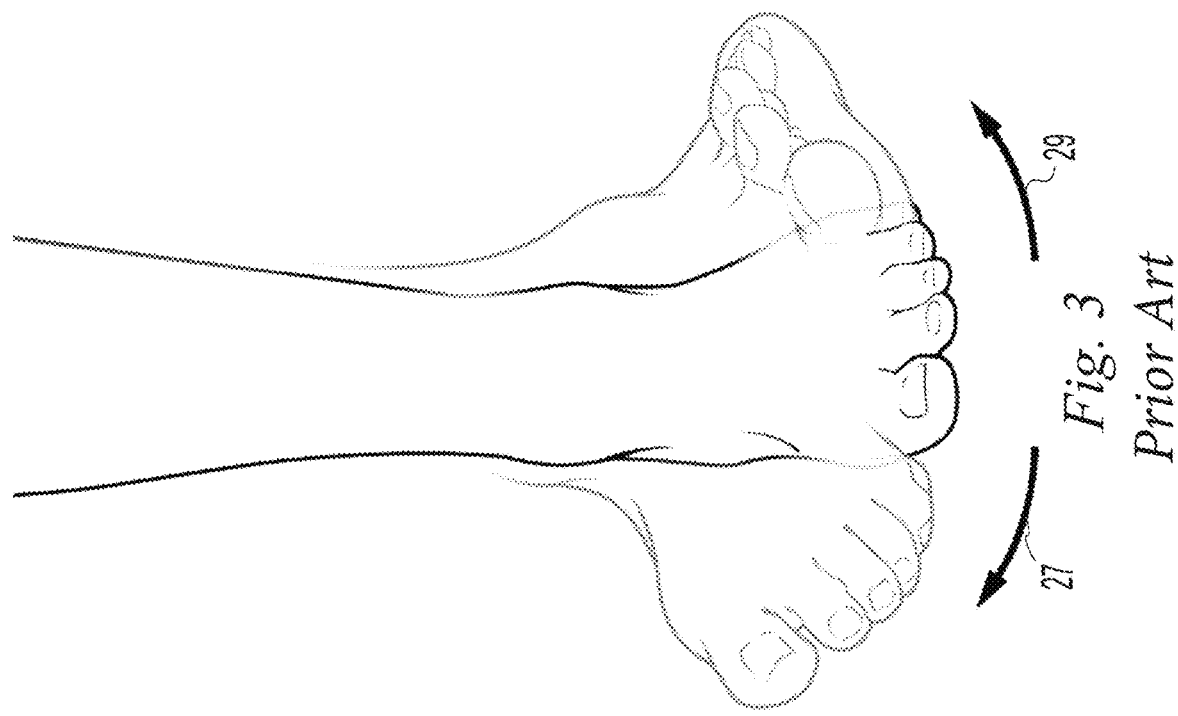
FIG. 3 is a coronal view of a foot illustrating inversion and eversion.

FIG. 3 illustrates inversion 27 in which the sole of the foot is tilted toward the sagittal plane or midline of the body and eversion 29 in which the sole of the foot is tilted away from the sagittal plane.

FIGS. 4-10 illustrate the arrangement of the bones within the foot 30. A right foot is illustrated. Beginning at the proximal aspect of the foot, the heel bone or calcaneus 32 projects plantar. The talus 34 is dorsal to the calcaneus 32 and articulates with it at the talocalcaneal or subtalar joint. Dorsally, the talus articulates medially with the tibia 36 and laterally with the fibula 38 at the ankle joint. Distal to the ankle are the navicular bone 40 medially and the cuboid bone 42 laterally which articulate with the talus and calcaneus respectively. The navicular bone 40 and cuboid bone 42 may also articulate with one another at the lateral side of the navicular bone and the medial side of the cuboid bone. Three cuneiform bones lie distal to the navicular bone and articulate with the navicular bone and one another. The first, or medial, cuneiform 44 is located on the medial side of the foot 30. The second, or intermediate, cuneiform 46 is located lateral of the first cuneiform 44. The third, or lateral, cuneiform 48 is located lateral of the second cuneiform 46. The third cuneiform 48 also articulates with the cuboid bone 42. Five metatarsals 50, 52, 54, 56, 58 extend distally from and articulate with the cuneiform and cuboid bones. The metatarsals are numbered from 1 to 5 starting with the first metatarsal 50 on the medial side of the foot and ending with the fifth metatarsal 58 on the lateral side of the foot 30. The first metatarsal 50 articulates with the first cuneiform 44 at a metatarsocuneiform (MTC) joint 51. The second metatarsal 52 articulates with the first, second and third cuneiforms 44, 46, 48 and may articulate with the first metatarsal as well. Five proximal phalanges 60, 62, 64, 66, 68 extend distally from and articulate with the five metatarsals respectively. The first proximal phalanx 60 articulates with the first metatarsal 50 at a metatarsophalangeal (MTP) joint 61. One or more distal phalanges 70, 72, 74, 76, 78 extend distally from the proximal phalanges. The first metatarsal 50, first proximal phalanx 60, and, first distal phalanx 70 together are referred to as the first ray of the foot. Similarly, the metatarsal, proximal phalanx, and distal phalanges corresponding to the lesser digits are referred to as the second through fifth rays respectively.

Figure 5:
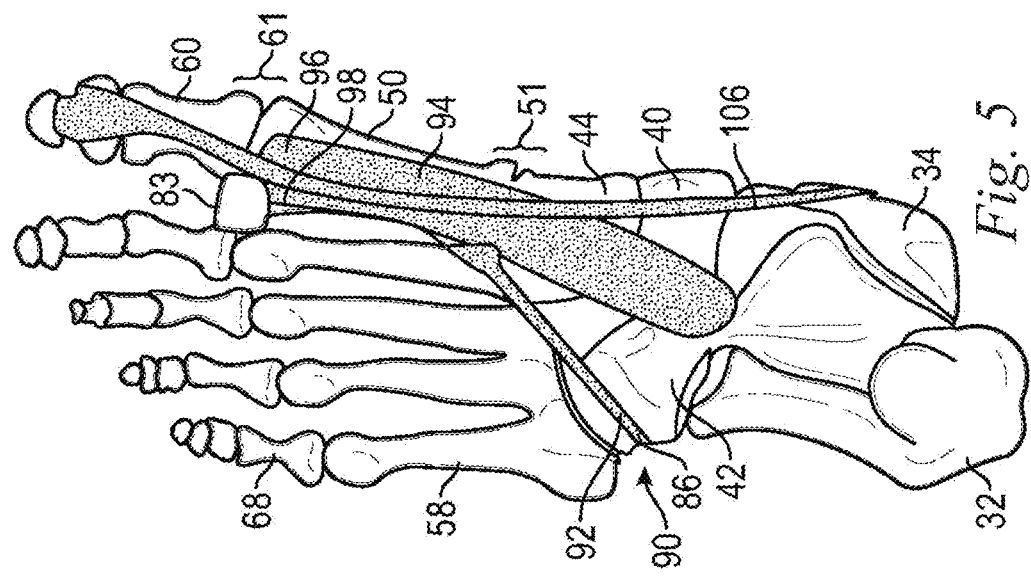
FIG. 5 is a plantar view illustrating bones, tendons, and ligaments of the foot.
Figure 4:
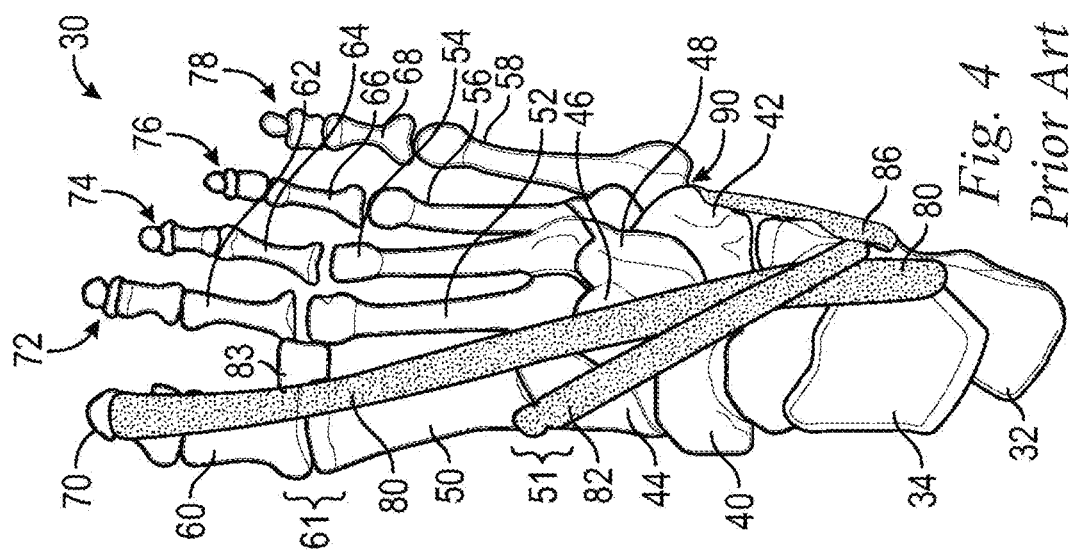
FIG. 4 is a dorsal view illustrating bones, tendons, and ligaments of the foot.
Figure 6:
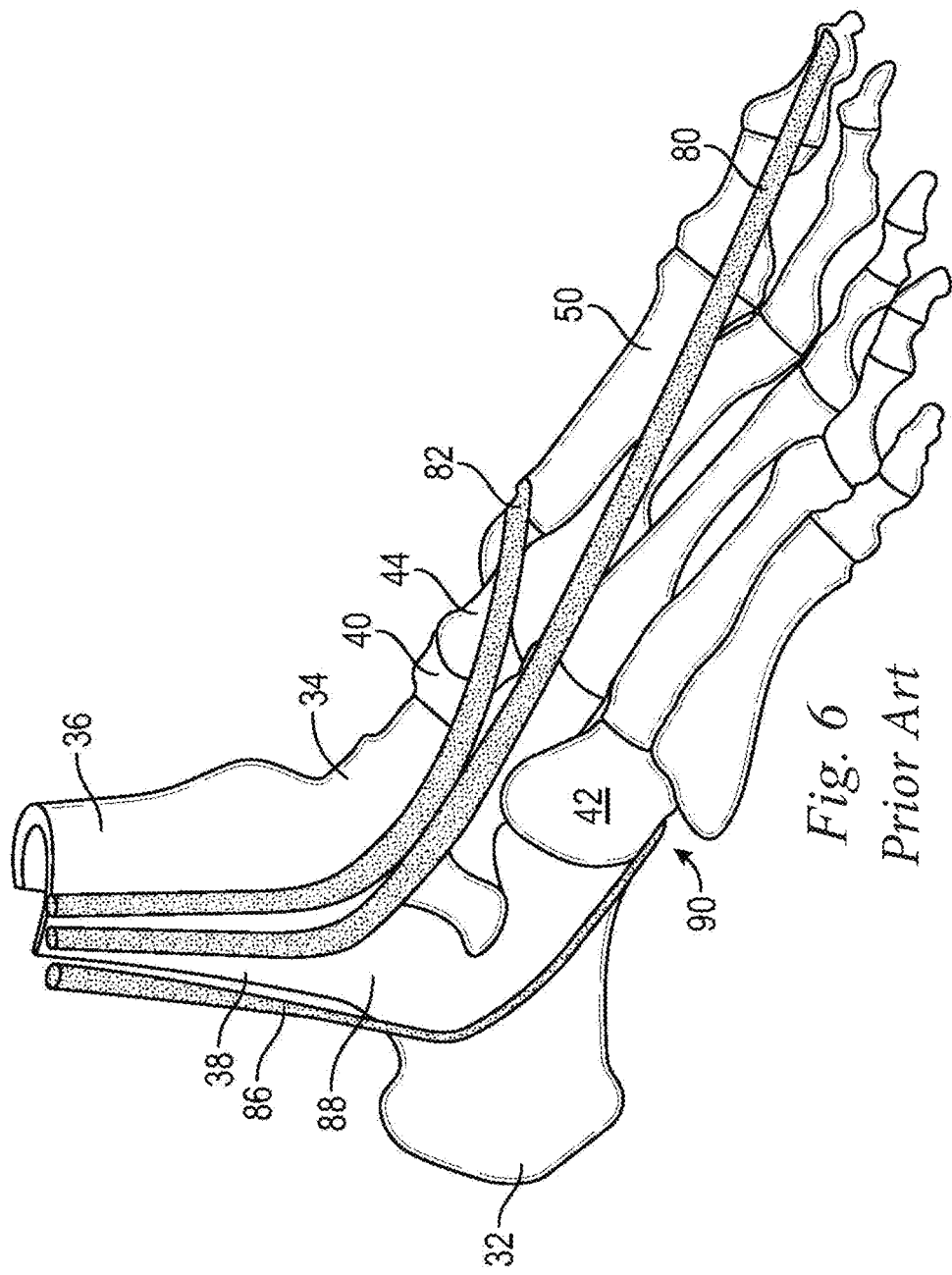
FIG. 6 is a perspective view illustrating bones, tendons, and ligaments of the foot.
Figure 9:
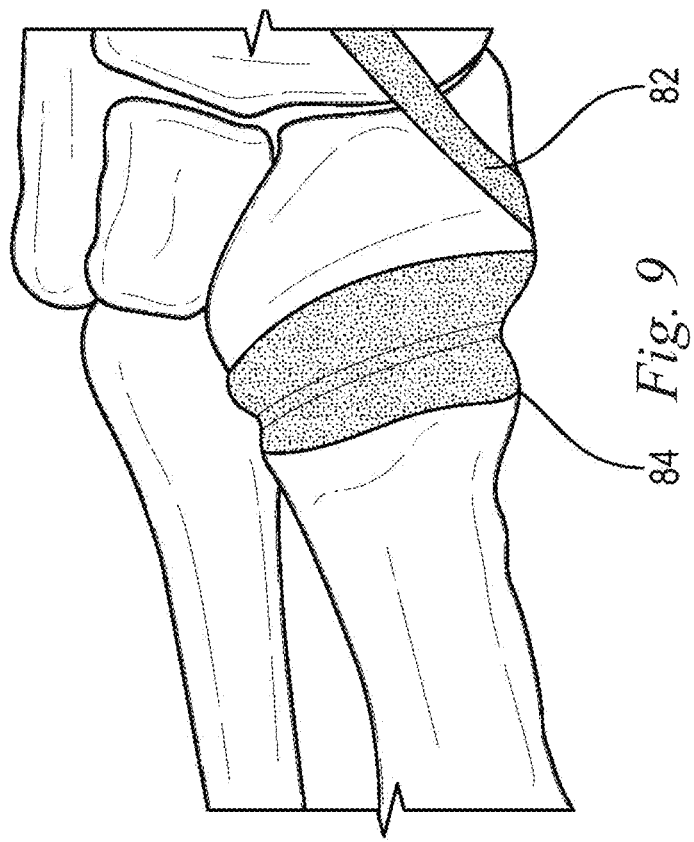
FIG. 9 is a dorsal view of the MTC joint of the first ray of the foot.
Figure 10:
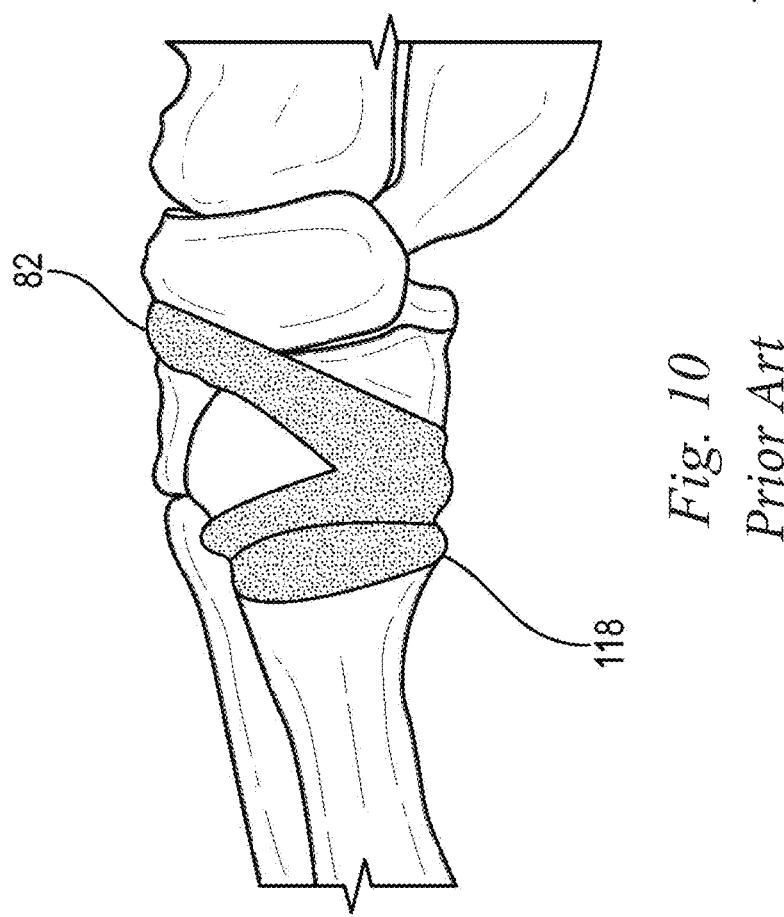
FIG. 10 is a medial view of the MTC joint of the first ray of the foot.

FIG. 4 is a dorsal view illustrating bones, tendons and ligaments of the foot. Plantar structures illustrated in FIG. 5 are omitted from FIG. 4 for clarity. The extensor hallucis longus muscle originates in the anterior portion of the leg, the extensor hallucis longus tendon 80 extends distally across the ankle and along the first ray to insert into the base of the distal phalanx 70. The tibialis anterior muscle originates in the lateral portion of the leg and the tibialis anterior tendon 82 extends distally across the ankle and inserts into the first cuneiform 44 and first metatarsus 50 at the first MTC joint 51 where it contributes to the MTC capsular structure 84 (FIGS. 9 and 10). A transverse intermetatarsal ligament 83 inserts into the capsule of the MTP joint such that it connects the heads of the first through fifth metatarsal bones. In FIGS. 4 and 5, only the connection between the first and second metatarsal bones 50, 52 is shown.

Figure 8:
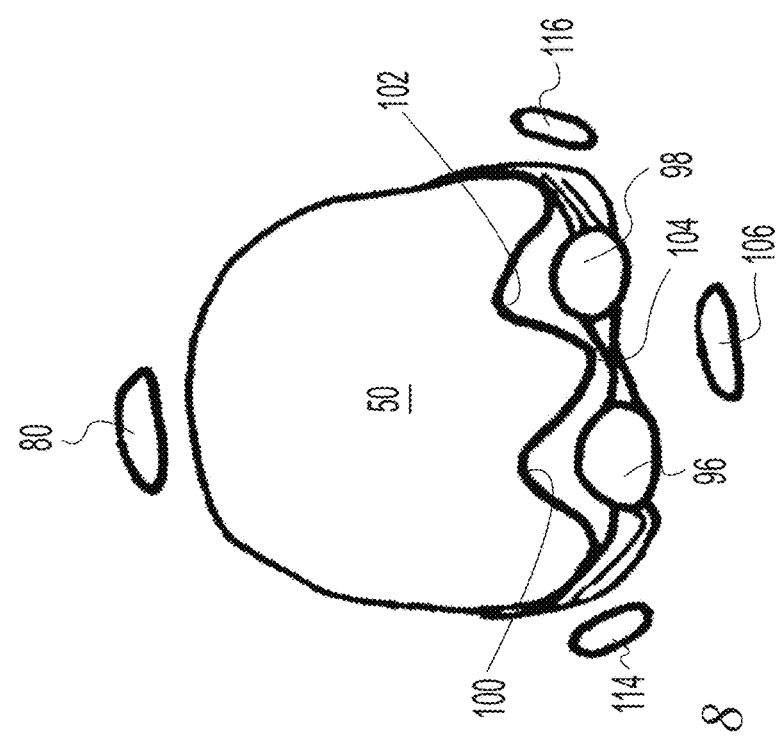
FIG. 8 is a sectional view taken along line 8-8 of FIG. 7.

FIG. 5 is a plantar view illustrating bones, tendons, and ligaments of the foot. Dorsal structures shown in FIG. 4 are omitted from FIG. 5 for clarity. The peroneus longus muscle originates at the head of the fibula and its tendon 86 passes posteriorly around the lateral malleolus 88 of the ankle, around the cuboid notch 90 on the lateral side of the cuboid bone 42, along the peroneal sulcus 92 on the plantar surface of the cuboid bone 42, and inserts into the first metatarsal 50. The flexor hallucis brevis muscle 94 originates from the cuboid 42 and third cuneiform 48 and divides distally where it inserts into the base of the proximal phalanx 60. Medial and lateral sesamoid bones 96, 98 are present in each portion of the divided tendon at the MTP joint 61. The sesamoids 96, 98 articulate with the plantar surface of the metatarsal head in two grooves 100, 102 separated by a rounded ridge, or crista 104 (FIG. 8). The flexor hallucis longus muscle originates from the posterior portion of the fibula 38. The flexor hallucis longus tendon 106 crosses the posterior surface of the lower end of the tibia, the posterior surface of the talus, runs forward between the two heads of the flexor hallucis brevis 94, and is inserted into the base of the distal phalanx 70 of the great toe.

Figure 7:
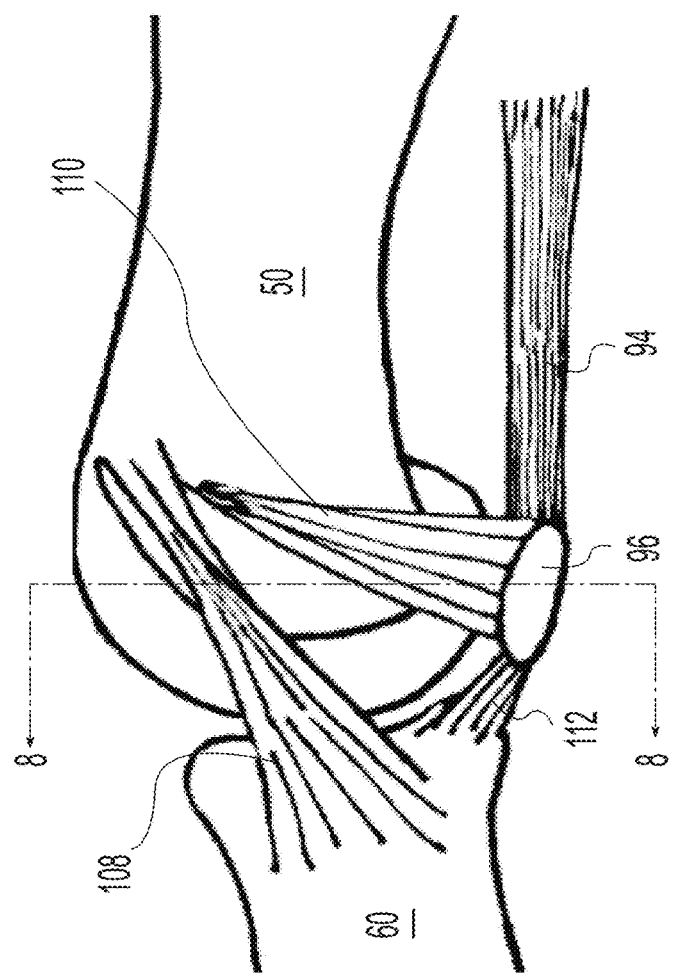
FIG. 7 is a medial view of the MTP joint of the first ray of the foot.

FIG. 7 is a medial view of tendons at the MTP joint 61 of the first ray. A medial collateral ligament 108 originates from the head of the first metatarsus 50 and inserts into the proximal phalanx 60. A medial metatarsosesamoid ligament 110 originates from the head of the first metatarsus 50 and inserts into the medial sesamoid bone 96. Similar collateral and metatarsosesamoid ligaments are found on the lateral side of the first MTP joint. The flexor hallucis brevis 94 is shown inserting into the sesamoids 96, 98. Ligamentous fibers extend further distally in the form of a phalangealsesamoid ligament 112 from the sesamoids to the proximal phalanx 60.

FIG. 8 is a sectional view taken along line 8-8 of FIG. 7 showing the metatarsal head 50, the tendon of the extensor hallucis longus 80, the medial and lateral sesamoid bones 96, 98, the grooves 100, 102 in which the sesamoids articulate, the crista 104 separating the grooves, the flexor hallucis longus 106, the abductor hallucis 114, and the adductor hallucis 116.

FIG. 9 is a dorsal view showing the dorsal capsular structure 84 of the MTC joint 51 of the first ray including the insertion of the tibialis anterior tendon 82.

FIG. 10 is a medial view of the MTC joint 51 of the first ray showing the medial capsular structure 118 including the insertion of the tibialis anterior tendon 82.

Figure 12:
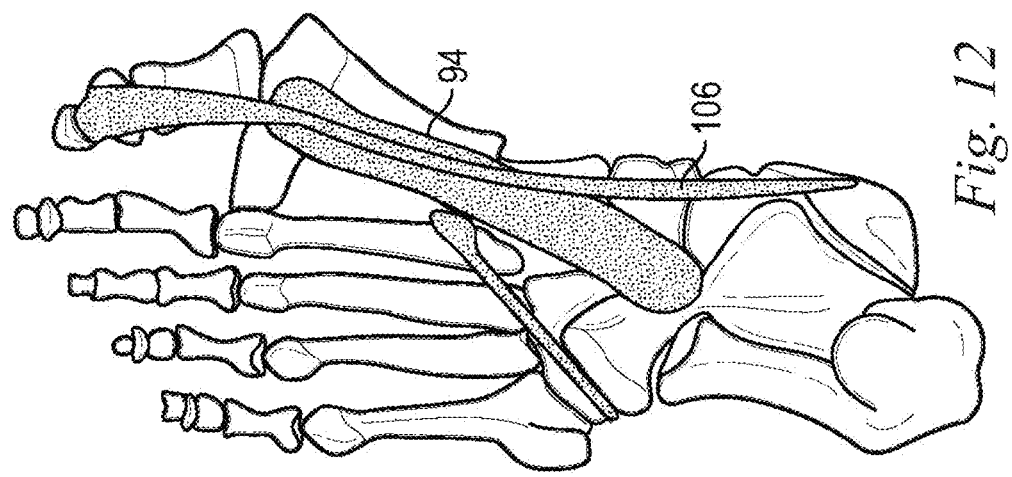
FIG. 12 is a plantar view illustrating deformity of the foot.
Figure 11:
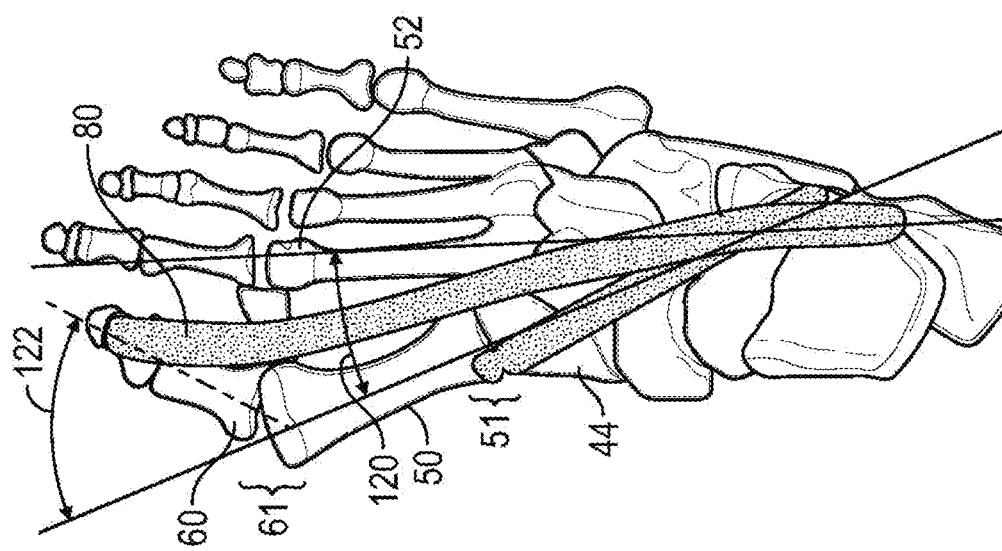
FIG. 11 is a dorsal view illustrating deformity of the foot.
Figure 13:
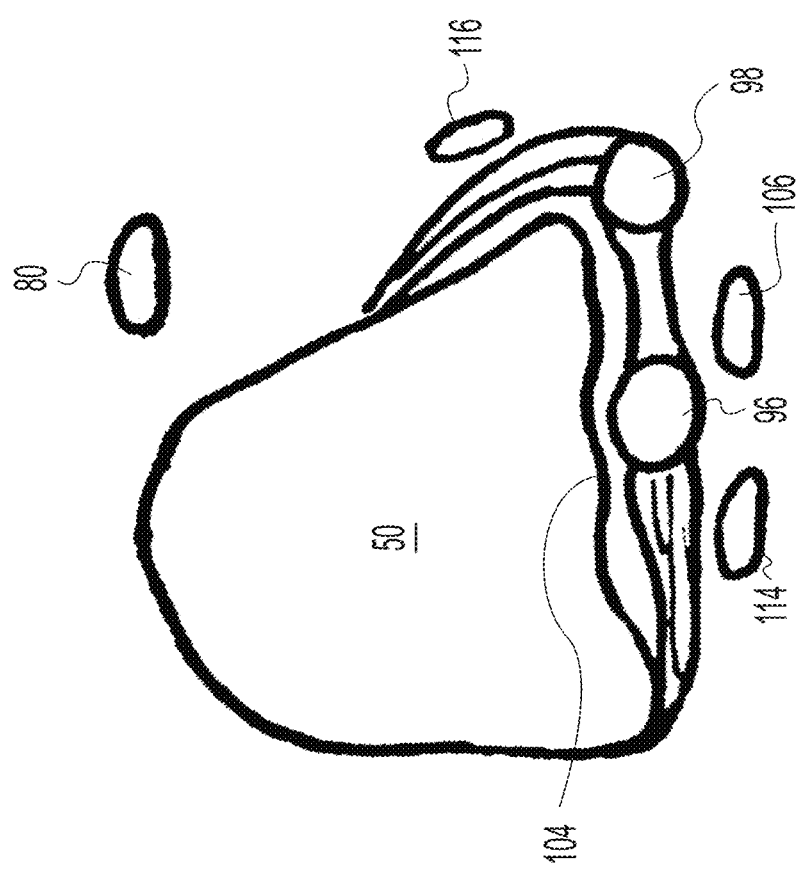
FIG. 13 is a sectional view similar to that of FIG. 8 but illustrating deformity of the foot.

FIGS. 11-13 illustrate deformities of the first ray. In a dorsal view, as shown in FIG. 11, an intermetatarsal angle (IMA) 120 may be measured between the longitudinal axes of the first and second metatarsal bones 50, 52. The angle is considered abnormal when it is 9 degrees or greater and the condition is known as metatarsus primus varus (MPV) deformity. A mild deformity is less than 12 degrees, a moderate deformity is 12-15 degrees, and a severe deformity is greater than 15 degrees. Similarly, a hallux valgus angle (HVA) 122 may be measured between the longitudinal axes of the first metatarsus 50 and the first proximal phalanx 60 at the MTP joint 61. The angle is considered abnormal when it is 15 degrees or greater and the condition is known as a hallux valgus (HV) deformity. A mild deformity is less than 20 degrees, a moderate deformity is 20 to 40 degrees, and a severe deformity is greater than 40 degrees.

MPV and HVA often occur together as shown in FIGS. 11-12. As the deformities progress several changes may occur in and around the MTC and MTP joints. Referring to FIG. 13, as the IMA and HVA increase, the extensors 80, flexors 106, abductors 114, and adductors 116 of the first ray (along with the sesamoids 96, 98) are shifted laterally relative to the MTP joint. The tendons exert tension lateral to the MTP joint creating a bow string effect (as best seen in FIGS. 11 and 12) that tends to cause the deformities to increase. The relative shift of the sesamoids 96, 98 is often accompanied by erosion of the crista 104. The abnormal muscle forces cause the metatarsus 50 to pronate, or in other words, rotate so that the dorsal aspect of the bone moves medially and the plantar aspect moves laterally. Rotation in the opposite direction is referred to as supination. Soft tissues on the medial side of the MTP joint and lateral side of the MTC joint attenuate, through lengthening and thinning, thus weakening the capsule and permitting the deformities to progress. Soft tissues on the opposite sides of the capsule tend to shorten, thicken and form contractures making it difficult to reduce the joints to their normal angular alignment.

More generally, deformities of the first ray may include metatarsus primus varus, hallux valgus, abnormal pronation, abnormal supination, abnormal dorsiflexion, and/or abnormal plantar flexion. These deformities correspond to three different planar rotations. Metatarsus primus varus and hallux valgus result from rotations in the transverse plane 24. Pronation and supination are rotation in the coronal plane 10. Dorsiflexion and plantar flexion are rotation in the sagittal plane.

The terms "suture" and "suture strand" are used herein to mean any strand or flexible member, natural or synthetic, able to be passed through material and useful in a surgical procedure. The term "transverse" is used herein to mean crossing as in non-parallel.

Figure 14:
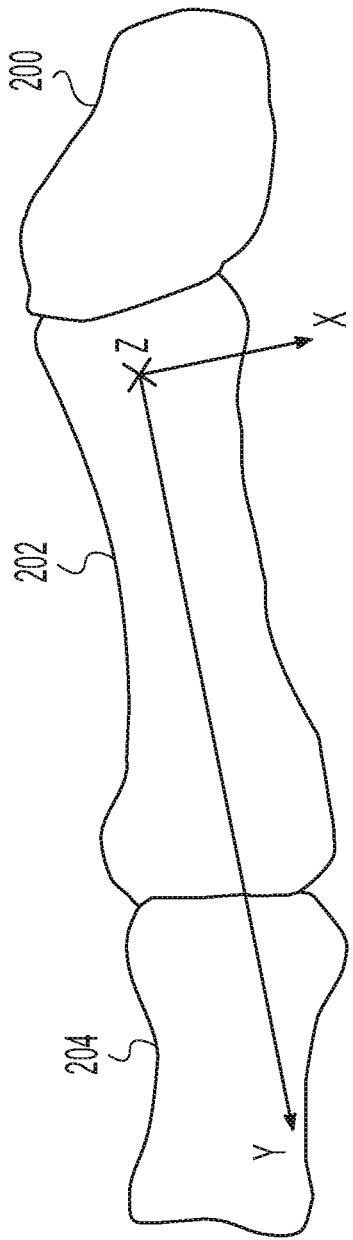
FIG. 14 is dorsal view of bones of the first ray of a human foot illustrating coordinate axes according to the present invention.
Figure 15:
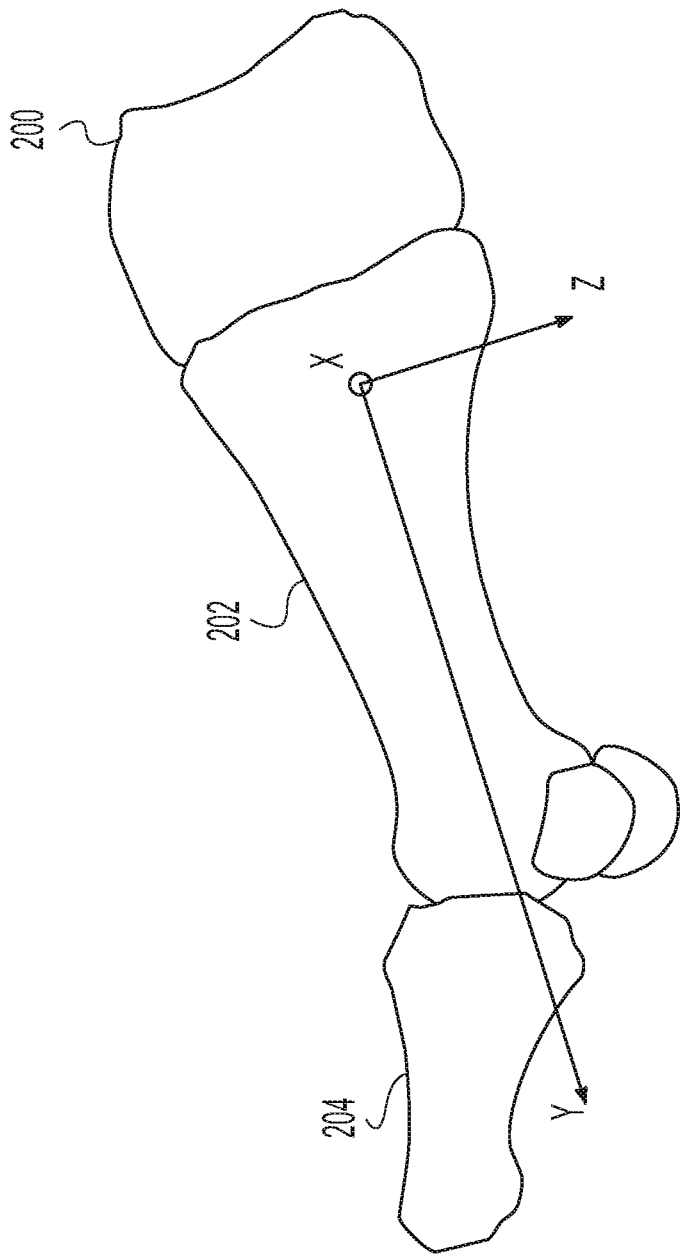
FIG. 15 is a medial view of the bones of FIG. 14 illustrating coordinate axes according to the present invention.

The present invention provides methods and devices for performing an osteotomy. In a method according to the present invention, a desired positional change between two bone portions is predetermined and then the bone is cut to allow the bone portions to be repositioned in the new position. By way of illustrative example, FIGS. 14 and 15 illustrate the medial cuneiform 200, first metatarsus 202, and proximal phalanx 204 of the first ray of a human foot with overlying coordinate axes. FIG. 14 is a dorsal view, looking down, on the first ray. FIG. 15 is a medial view, looking from the medial side, of the first ray. The Z-axis is positive plantar, the X-axis is positive medial, and the Y-axis is positive distal. The Y-axis is parallel to the anatomic axis of the first metatarsus. The Y-Z plane is a local, first metatarsal sagittal plane and in a healthy foot is rotated slightly medial about the Z-axis relative to the sagittal plane of the body. The X-Y plane is a local, first metatarsal transverse plane and in a healthy foot is rotated slightly dorsal about the X-axis relative to the transverse plane of the body due to the natural angle of the foot. The X-Z plane is a local, first metatarsal coronal plane and in a healthy foot is rotated slightly anterior about the X-axis relative to the coronal plane of the body due to the natural angle of the foot.

Figure 16:
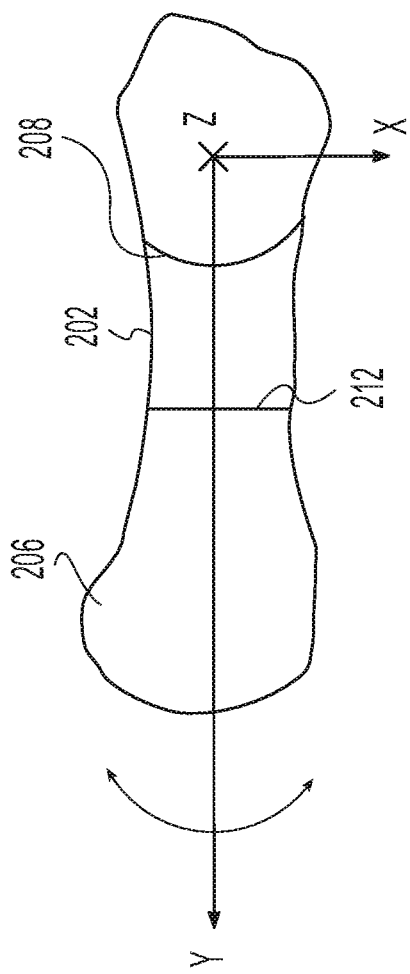
FIG. 16 is a dorsal view of a metatarsus illustrating coordinate axes according to the present invention.
Figure 17:
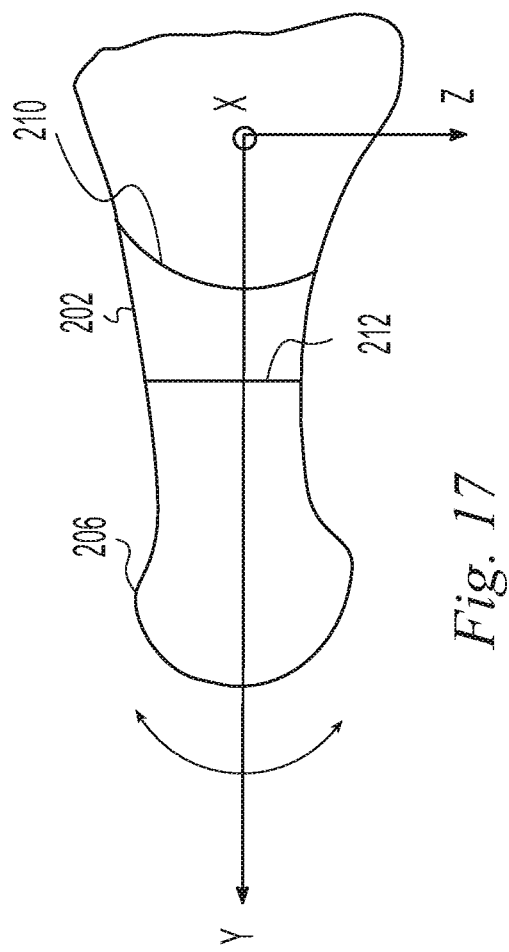
FIG. 17 is a medial view of the metatarsus of FIG. 16 illustrating coordinate axes according to the present invention.
Figure 18:
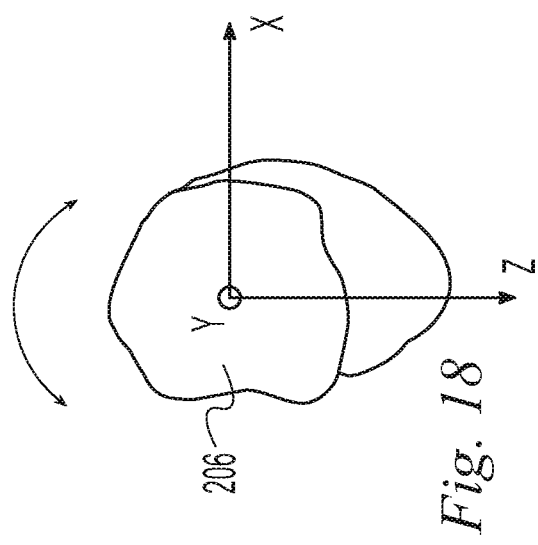
FIG. 18 is an anterior view of the metatarsus of FIG. 16 illustrating coordinate axes according to the present invention.

FIGS. 16-18 illustrate the metatarsus 202 alone with the coordinate axes of FIGS. 14 and 15. Rotation about each of the axes is shown. Referring to FIG. 16, rotation in the X-Y plane about the Z-axis results in a change in the IMA. Referring to FIG. 17, rotation in the Y-Z plane about the X-axis results in a change in dorsiflexion/plantarflexion. Referring to FIG. 18, rotation in the X-Z plane about the Y-axis results in a change in pronation/supination. In the case of an osteotomy, a cut is made in a bone to change the position of one portion of the bone relative to another portion. For example, in a metatarsus 202, it may be desirable to change the position of the distal metatarsal head 206 relative to the proximal portion of the bone. As shown in FIG. 16, a cylindrical cut 208, also referred to as a crescentic cut, concentric with the Z-axis allows a change in IMA by rotating the cut surfaces relative to one another about the Z-axis. Likewise, as shown in FIG. 17, a cylindrical cut 210 concentric with the X-axis allows a change in flexion angle by rotating the cut surfaces relative to one another about the X-axis. Similarly, a planar cut 212 parallel to the X-Z plane (FIGS. 16 and 17) allows a change in pronation/supination by rotating the cut surfaces about the Y-axis (FIG. 18).

It is possible to create an oblique cut, i.e. a cut angled relative to two or three axes, that results in simultaneous angular changes in 2 or 3 anatomic planes. For example, referring to FIG. 19A, an initial position 214 of a bone portion axis can be changed by rotating the bone portion about two axes to a new position 216. Using the illustrative example of FIGS. 14-18, this would correspond to plantar flexing the metatarsus by an angular amount 218 corresponding to a plantar displacement 220 of the distal head 206 and decreasing the IMA an angular amount 222 corresponding to a lateral displacement 224 of the distal head 206. These two motions to move to the new position 216 can be resolved to a bi-planar rotation plane 226 having a bi-planar rotation axis 228 normal to the bi-planar rotation plane 226. In other words, cutting the bone and relatively rotating the resulting bone portions in the bi-planar rotation plane 226, e.g. such as about the bi-planar rotation axis 228, will simultaneously change the relative plantar flexion and IMA of the bone portions. For any given combination of predetermined plantar displacement 220 and change in IMA 222, rotating the cut bone portions to achieve one of the changes will necessarily produce the other change due to the coupled motion about the bi-planar rotation axis 228. For example, repositioning the bone portions to reduce the IMA by the predetermined amount 222 will also result in the predetermined plantar displacement 220. For many combinations of correction, the bone cut may be a crescentic cut coaxial with the bi-planar rotation axis 228 or a planar cut normal to the bi-planar rotation axis 228. For other combinations, the angle of the bi-planar rotation axis 228 may make either a crescentic cut or a planar cut more practical.

Figure 19A:
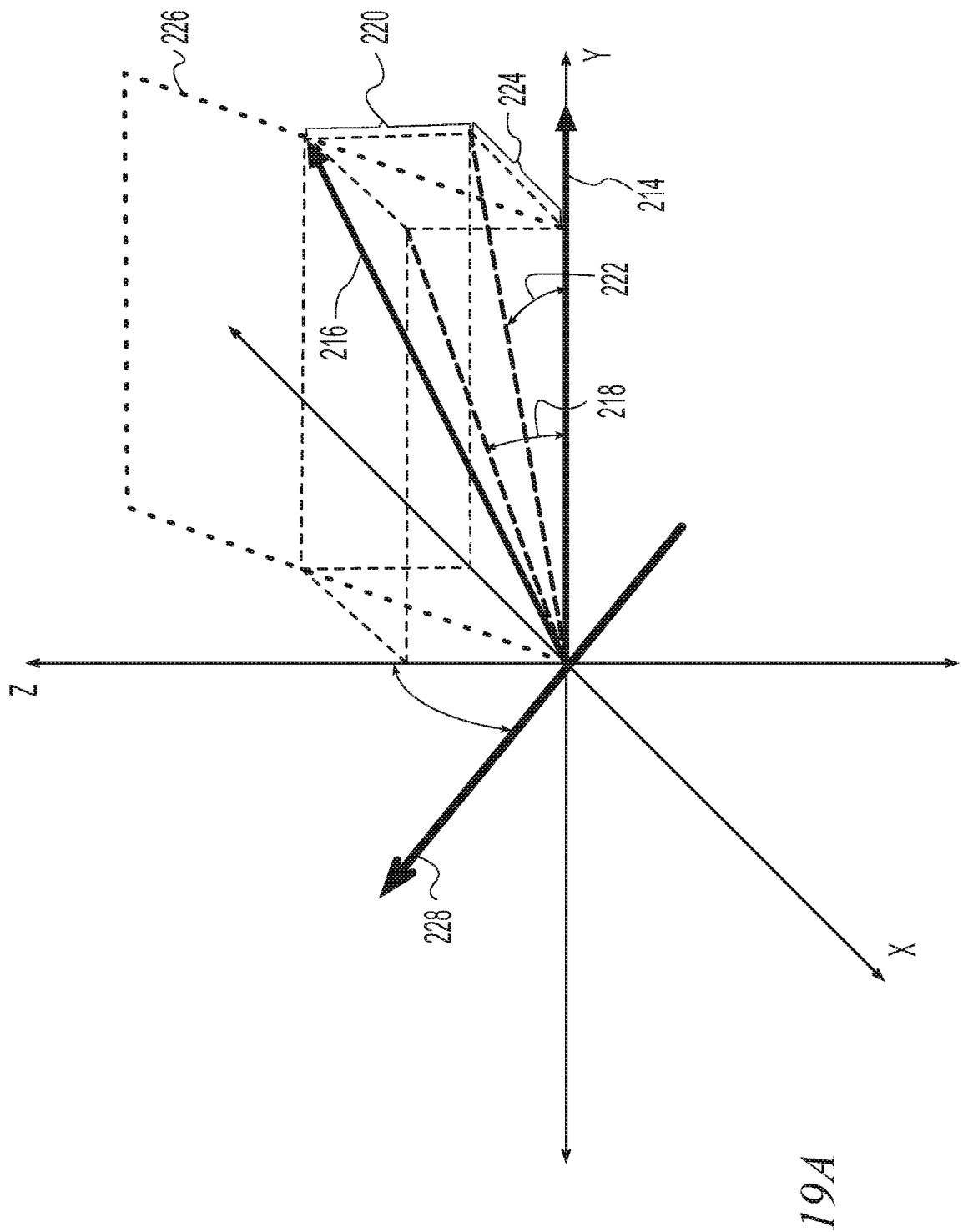
FIGS. 19A-19D are schematic views illustrating the orientation of a metatarsus before and after an osteotomy according to the present invention.
Figure 19B:
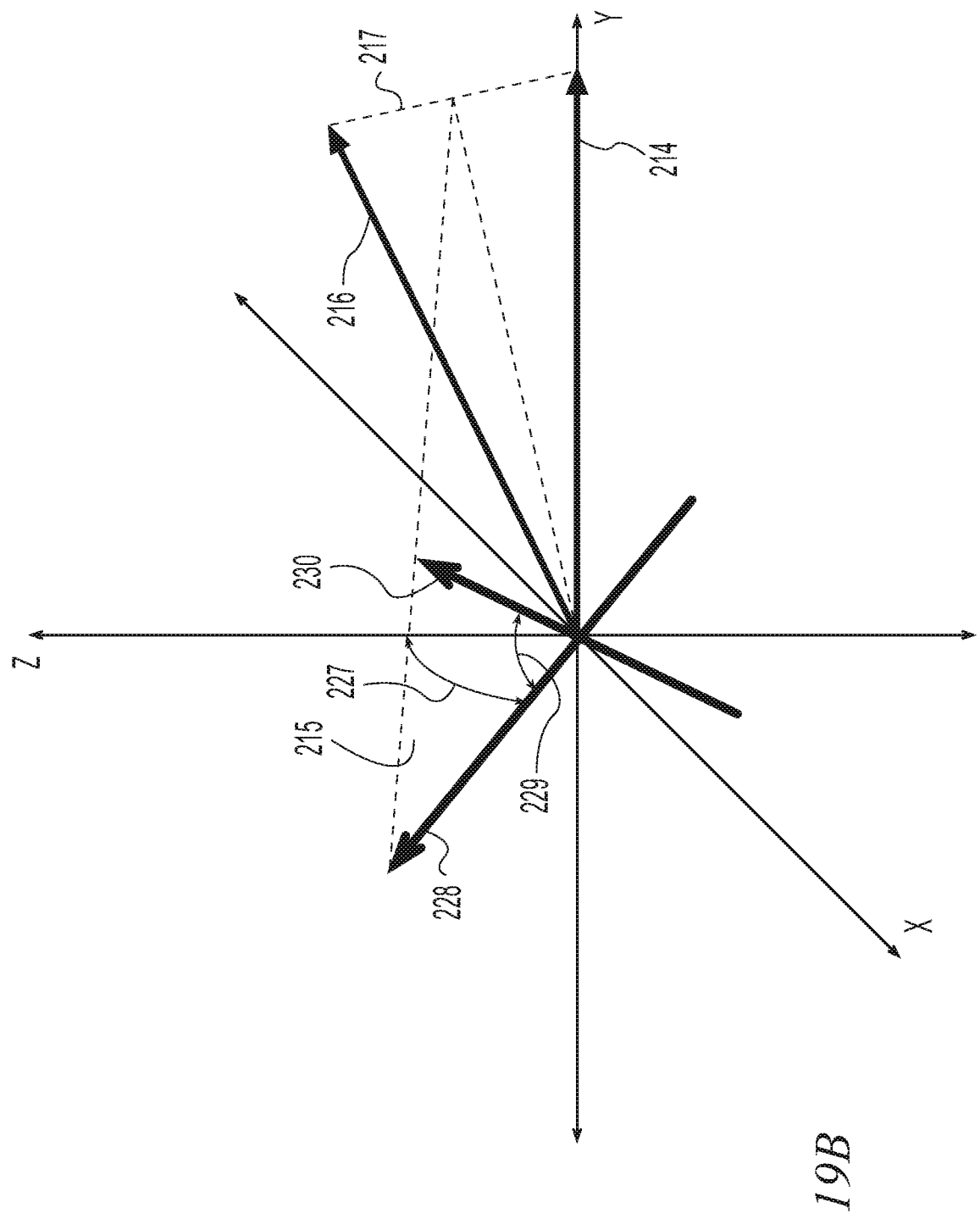

Referring to FIGS. 19A and 19B, an additional rotation about the bone axis from the initial position 214 to the new position 216 may be included and when combined with the other two motions results in a tri-planar rotation axis 230 about which a rotation will result in a tri-planar correction. In the illustrative example of FIGS. 14-18, this additional rotation corresponds to a change in pronation/supination of the metatarsus about its anatomic axis. In FIG. 19B, a first plane may be constructed containing the bi-planar rotation axis 228 and the initial position 214 of the bone portion axis. A second plane may be constructed containing the bi-planar rotation axis 228 and the new position 216 of the bone portion axis. A bisector plane 215 contains the bi-planar rotation axis 228, the tri-planar rotation axis 230 and is angularly spaced half-way between the initial and new positions 214, 216.

Figure 19D:
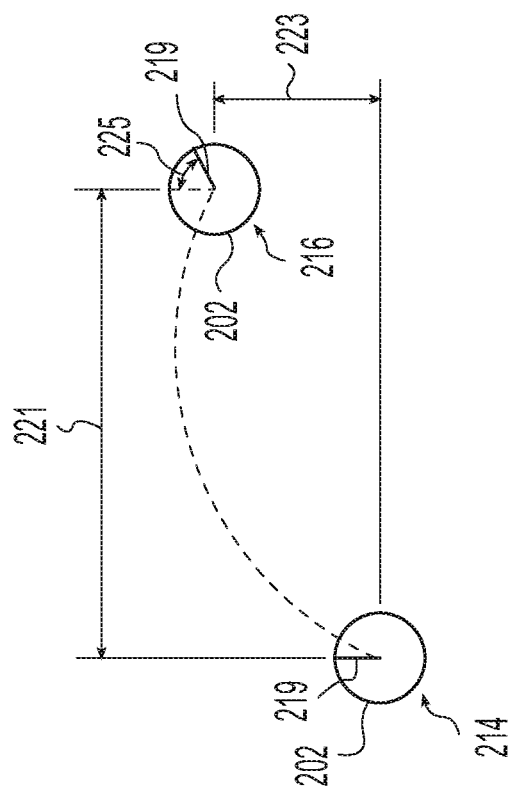
Figure 19C:
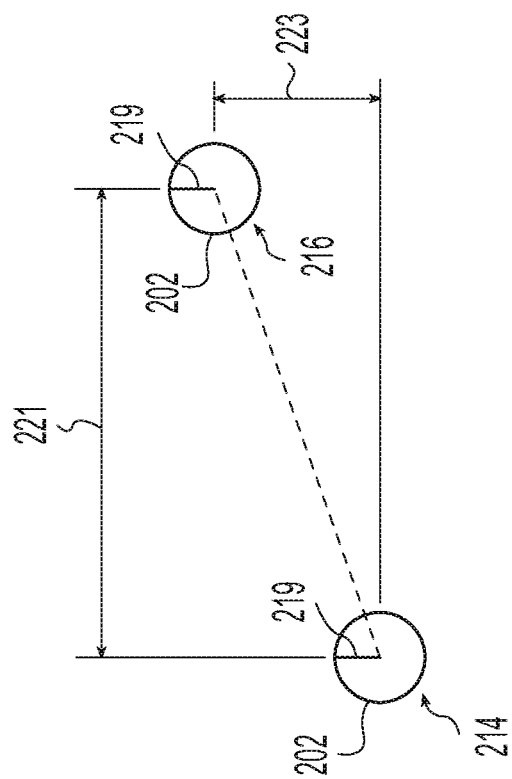

FIG. 19C illustrates the motion of the end of the metatarsus 202 in a motion plane 217 (FIG. 19B) perpendicular to the bisector plane 215 for the case of rotation about the bi-planar rotation axis 228. A reference mark 219 is included to illustrate the pronation/supination of the bone. With rotation about the bi-planar rotation axis 228, the end of the metatarsus translates from the initial position 214 to the new position 216 resulting in a medial/lateral displacement 221 and a dorsal/plantar displacement 223 but without any change in pronation/supination; i.e. without any rotation about the anatomic longitudinal axis.

FIG. 19D illustrates the motion of the end of the metatarsus 202 in the motion plane 217 for the case of rotation about the tri-planar rotation axis 230. With rotation about the tri-planar rotation axis 230, the end of the metatarsus translates medial/lateral 221, translates dorsal/plantar 223 and rotates 225 in pronation/supination from the initial position 214 to the new position 216.

Referring to FIG. 19B, the bi-planar rotation axis 228 lies in the X-Z plane at an angle θ 227 relative to the Z-axis. The tri-planar rotation axis 230 lies in the bisector plane 215 at an angle Φ 229 from the bi-planar rotation axis 228. Letting α=the change in IMA 222, ω=the change in pronation/supination 225, L=the metatarsal axis length from the rotation axis to the joint line of the MTP joint, C=the dorsal/plantar displacement 220 of the metatarsal head, and R=the ratio C/L, then θ=fn(R, α) and Φ=fn(α, ω) using vector transformations as is known in the art.

By determining the current position of an abnormally positioned metatarsus and the desired final position, a desired positional change in each plane may be determined. The current and desired positions may be determined by medical imaging, computer modeling, manual measurement, or other techniques as is known in the art. The desired positional change may be expressed as an angular change or, for a given position relative to the osteotomy location, it may be expressed as a displacement. For example, in the illustrative example of an osteotomy of the first metatarsus, it may be desirable to express one or more of the positional changes in terms of a displacement of the distal metatarsal head 206 such as, e.g., the plantar displacement 220 of FIG. 19A. As long as the distance from the metatarsal head to the rotation axis of the osteotomy is known, the positional change may be expressed as either an angle or a displacement. In the following examples, for example, plantar flexion is expressed as an amount of plantar displacement of the distal head of the metatarsus, based either a gauged metatarsal axis length L or an estimated metatarsal axis length L determined as the difference between an average metatarsus overall length and a gauged distance from the proximal end of the metatarsus to the osteotomy.

An illustrative method according to the present invention produces an osteotomy between a first bone portion and a second bone portion. The bone portions define a first relative position between them. The method includes defining a rotation axis or a corresponding rotation plane in fixed relationship to the bone, referencing a cutter to the rotational axis or plane, cutting the bone to mobilize the first and second bone portions relative to one another, and rotating the first bone portion relative to the second bone portion within the rotation plane and/or about the rotational axis. The rotational axis and plane incorporate a desired positional change in one or more planes, preferably in two or three anatomic planes. For example, to reposition a first portion of a bone relative to a second portion of the bone, an axis guide may be provided that defines one or more rotational axes. Each rotational axis may incorporate an angular change in one or more anatomic reference planes. Each rotational axis may be incorporated into the axis guide by, e.g., calculating angles θ 227 and Φ 229 as described above for a particular combination of corrections. The axis guide may then be modeled along with features operable to orient the guide relative to anatomic reference planes. Each rotational axis may then be superimposed on the model relative to the same anatomic reference planes and be used to define a feature such as a hole, pin, slot, groove, intersecting surfaces, or other suitable features corresponding to the rotational axis or corresponding rotational plane. A cutter may be referenced to one of the rotation axes or rotational planes and guided to mobilize the first and second bone portions relative to one another. The bone portions may then be relatively rotated within the rotational plane and/or about the rotation axis, to realize the angular change in the one or more reference planes. In one example, the cutter may be linked directly to the axis guide. In another example, the axis guide may be used to provide a feature such as a hole or pin in the bone defining the rotation axis which is referenced by the cutter. The axis guide may be removed prior to referencing the cutter to the rotation axis. For example, the axis guide may include a guide hole corresponding to each rotation axis and the guide hole may be used to place a pin in the bone aligned with a desired rotation axis and the axis guide may then be removed. A cutter may then engage the pin for rotation about the pin to create a cylindrical cut in the bone about which the bone portions may be relatively rotated. Alternatively, a cut guide defining a cut plane may be referenced to the pin. A cutter may then be guided in the cut plane to create a planar cut between the bone portions. The bone portions may then be rotated about the rotation axis. Alternatively, a cut guide defining one or more rotation planes corresponding to one or more predetermined multi-planar corrections may be provided. The cut guide may be referenced to the bone and used to guide a cutter to create a planar cut between the bone portions without first creating a rotation axis in or on the bone. In this case, the rotation plane or planes corresponding to the rotation axes are defined by the guide and the guide is positioned on the bone by aligning reference features of the guide with the bone to correctly orient the guide to correctly position the one or more rotation planes. The guide may then be used to guide a cutter directly to create a planar cut in the bone corresponding the to the desired rotation plane. The freed bone portions may then be rotated in the rotation plane to achieve the multi-planar correction.

Figure 21:
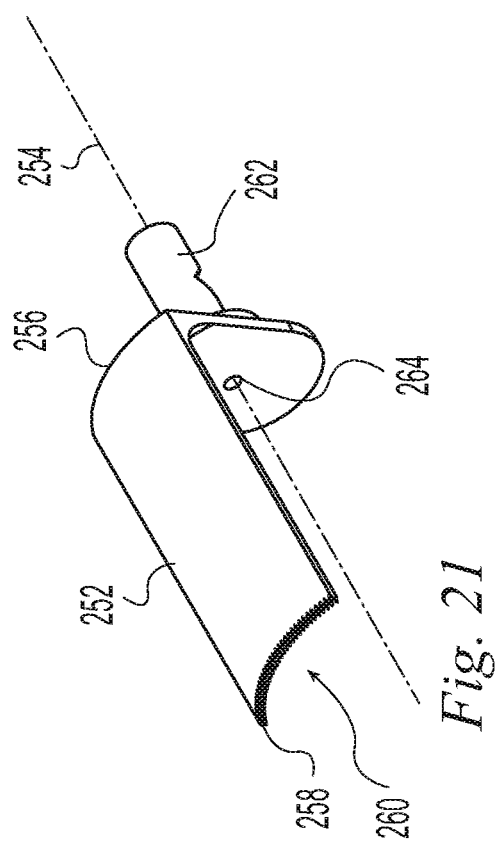
FIGS. 20 and 21 are isometric views of a saw blade according to the present invention.
Figure 20:
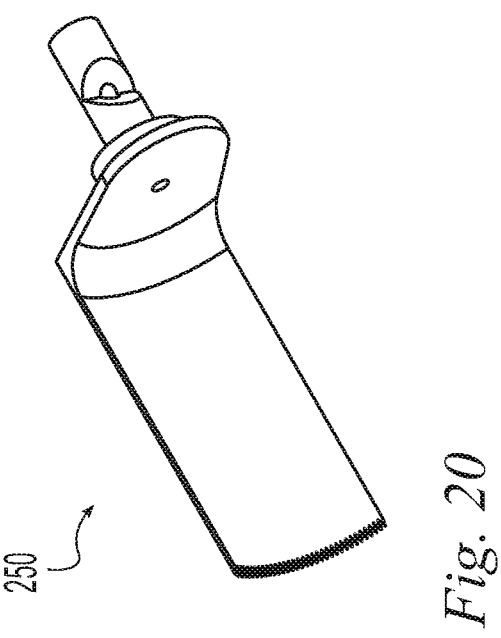
Figure 22:
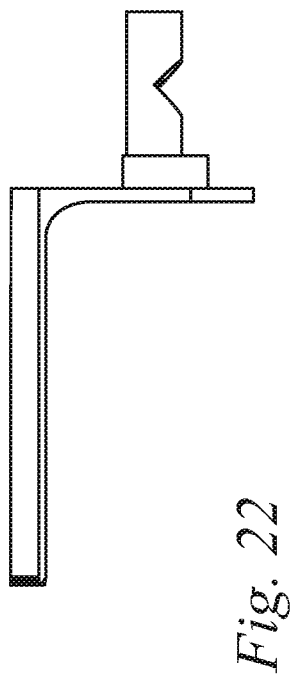
FIG. 22 is a side view of the saw blade of FIGS. 20 and 21.
Figure 27:
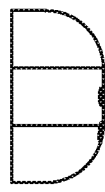
FIGS. 24-28 are orthographic views of the cut block of FIG. 23.
Figure 24:
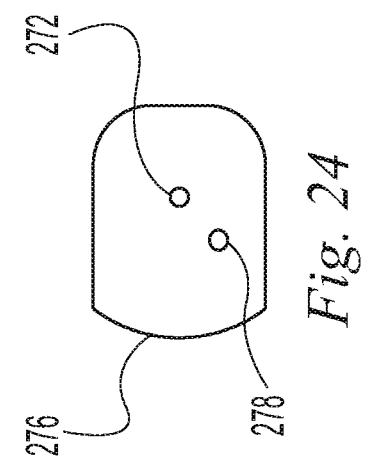
Figure 26:
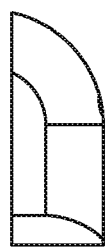
Figure 28:
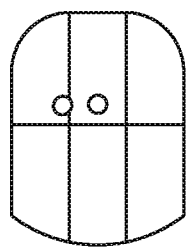
Figure 23:
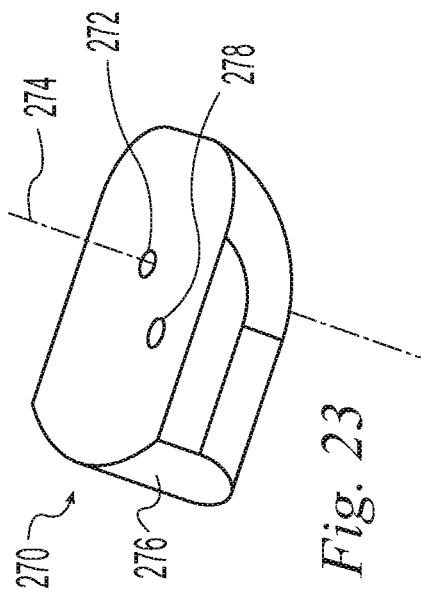
FIG. 23 is an isometric view of a cut block according to the present invention.
Figure 25:
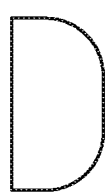

FIGS. 20-22 depict an illustrative crescentic blade 250. The blade 250 has a thin wall 252 forming a portion of a cylinder curved about a blade axis 254 and extending from a proximal end 256 to a distal end 258. Teeth 260 are formed on the distal end 258. The proximal end 256 is attached to a shaft 262 coaxial with the blade axis 254. The shaft 262 may be attached to a powered handpiece to rotate the blade about the blade axis and form a cylindrical cut in a bone. By using an oscillating motion, a cut transcribing an arc of a cylinder can be made. The shaft 262 may include an axial bore 264 coaxial with the blade axis 254 able to receive a pin in rotational engagement for guiding the blade in rotation about the pin.

FIGS. 23-28 depict an illustrative cut block 270. The cut block 270 has a bore 272 defining a rotation axis 274. The bore 272 is able to receive a pin in axial sliding and rotational relationship. The cut block includes a curved surface 276 defining at least a portion of a cylinder parallel to the rotation axis 274. The cut block 270 may be pinned to a bone by placing a pin through the bore 272 and into the bone. A second pin may be placed through a second bore 278 and into the bone to prevent the cut block from rotating about the first pin. A cutter, such as the crescentic blade 250 of FIGS. 20-22, may be guided to form a cut about the rotation axis 274 of the cut block by pressing the curved blade against the curved surface 276.

FIGS. 29-34 depict an illustrative blade guide 280. The blade guide 280 includes a shaft 282 having a bore 284 defining an axis 286 extending between a proximal end 288 and a distal end 290. A set screw 291 is contained in a hole transverse to the bore 284. The set screw 291 may be tightened to lock the blade guide 280 to a pin received in the bore 284. The blade guide 280 defines a plane 281, normal to the bore axis 286, for guiding a cutter, e.g. a saw blade, to make a planar cut in a bone. In the illustrative example of FIGS. 29-34, a surface 292 formed near the distal end 290 defines the plane. More particularly in the illustrative example of FIGS. 29-34, a pair of opposing surfaces defines a slot 294 between them able to receive a saw blade and constrain it to motion in a plane. The blade guide 280 is narrow proximally and wide distally to provide clearance for soft tissues while providing a wide slot 294 allowing the blade to be swept from side to side within the slot 294. The distal end 290 is offset 296 from the axis 286 so that the bore 284 can be placed on a pin in a bone and the distal end 290 be placed beside the bone. The distal end 290 is curved as seen in FIGS. 29 and 34 to accommodate the particular anatomy of the illustrative example for use on a metatarsus of a human foot.

FIGS. 35-41 depict an illustrative axis guide 310. The axis guide 310 is used to establish a rotation axis on a bone for guiding an osteotomy cut. The axis guide 310 includes at least one guide hole able to define a rotation axis on a bone. For example, the guide hole may be referenced directly. Alternatively, it may be used to guide a drill to form a hole in a bone such that the hole may be referenced to guide a cutter. Similarly, the guide hole may guide the placement of a pin that may be referenced to guide a cutter. When the guide is aligned with a bone, the guide hole defines a rotation axis corresponding to a positional change that may be produced by an osteotomy in which a cutter is referenced to the rotation axis. The position change may include changes in one or more anatomic planes. In the illustrative example of FIGS. 35-41, the axis guide 310 includes multiple guide holes, each guide hole defining a rotational axis corresponding to a different positional change between first and second bone portions in at least two anatomic reference planes. For example, the illustrative axis guide 310 of FIGS. 35-41 is configured for establishing rotational axes for a metatarsal osteotomy to produce a positional change in IMA, pronation, and plantar flexion. In the illustrative example of FIGS. 35-41, the plantar flexion is expressed on the guide as a change in plantar displacement of the distal head of the metatarsus. The axis guide 310 includes rows 312 and columns 314 of guide holes in which each guide hole corresponds to a unique combination of change in IMA, pronation, and plantarflexion. Indicia may be provided on the axis guide 310 to indicate the amount of change produced in one or more of IMA, pronation, and plantarflexion, using each guide hole. In the illustrative example of FIGS. 35-41, the guide holes define axes that are angled relative to one another in at least two rotational degrees of freedom.

In the illustrative example of FIGS. 35-41, the axis guide 310 may be one of a set of axis guides in which each axis guide has a fixed plantarflexion positional change applied to each guide hole. In the illustrative example of FIGS. 35-41, the particular axis guide 310 shown corresponds to a fixed plantarflexion positional change corresponding to 2.5 mm of plantar displacement of the distal head of the metatarsus for a rotational axis a predetermined distance from the distal head of the metatarsus. The setting of that predetermined distance is shown later in this disclosure. The positional change is expressed in terms of plantar displacement for convenience. For metatarsal osteotomies, a surgeon typically is interested in preserving the plantar position of the distal head of the metatarsus or offsetting it a fixed amount. Therefore, it is convenient to have guides with a fixed plantar change and variable IMA and pronation changes.

For the illustrative axis guide 310 of FIGS. 35-41, the guide hole 316 in the row labeled 0 degrees of pronation and the column labeled 15 degrees of IMA will establish a rotational axis to guide an osteotomy that when rotated to decrease the IMA by 15 degrees will also result in 0 degrees of pronation correction and a 2.5 mm plantar shift of the distal head of the metatarsus. Similarly, the guide hole 318 in the row labeled 5 degrees of pronation and 10 degrees of IMA will establish a rotational axis to guide an osteotomy that when reduced to decrease the IMA by 10 degrees will also result in 5 degrees of pronation correction and a 2.5 mm plantar shift of the distal head of the metatarsus. Axis guides may be provided that incorporate IMA changes corresponding to any clinically expedient amount, e.g., with the goal of reducing the IMA to fall within a normal anatomic range. Preferably axis guides are provided that incorporate an IMA reduction ranging from 0 to 25 degrees; more preferably from 5 to 15 degrees. The guides may incorporate pronation correction corresponding to any clinically expedient amount, e.g., with the goal of correcting pronation to fall within a normal anatomic range. Preferably axis guides are provided that incorporate a pronation correction ranging from 0 to 15 degrees; more preferably from 0 to 10 degrees. The guides may incorporate plantarflexion changes corresponding to any clinically expedient amount. Preferably axis guides are provided that incorporate a plantar shift ranging from 0 to 5 mm; more preferably 0 to 2.5 mm.

An alignment reference is provided to align the axis guide 310 to anatomic features of the bone so that the positional changes are referenced to the anatomic planes. An alignment reference may include a mark, line, plane, projection, or other suitable reference. In the illustrative example of FIGS. 35-41, a dorsal-plantar through hole 330 and a distal hole 332 are provided to receive dorsal and distal alignment rods 334, 336 that are used to align the axis guide 310. The dorsal-plantar hole 330 may extend through the axis guide 310, as shown, to permit the dorsal alignment rod 334 to be driven through the axis guide 310 and into underlying bone to fix the axis guide 310 to the bone. It is advantageous to offset the holes 330, 332 medial-laterally as shown in FIGS. 37 and 40 so that the alignment rods 334, 336 do not collide. The distal alignment rod 336 may include an optional plantar directed pointer 338 at its distal end as an alignment aid. For example, the distal end of the distal alignment rod 336 may be bent to create the pointer 338. The plantar surface 340 of the axis guide 310 is concave medial-laterally to help stabilize it as it sits on the dorsal surface of a bone. An additional fixation hole 342 through the axis guide 310 may be used to provide additional fixation of the axis guide 310 to an underlying bone.

FIGS. 42-54 depict an illustrative method according to the invention. In the Illustrative example of FIGS. 42-54, the illustrative instruments of FIGS. 20-41 are shown in use to perform an osteotomy on a metatarsus of the first ray of a human foot for changing the alignment of the first ray.

Figure 42:
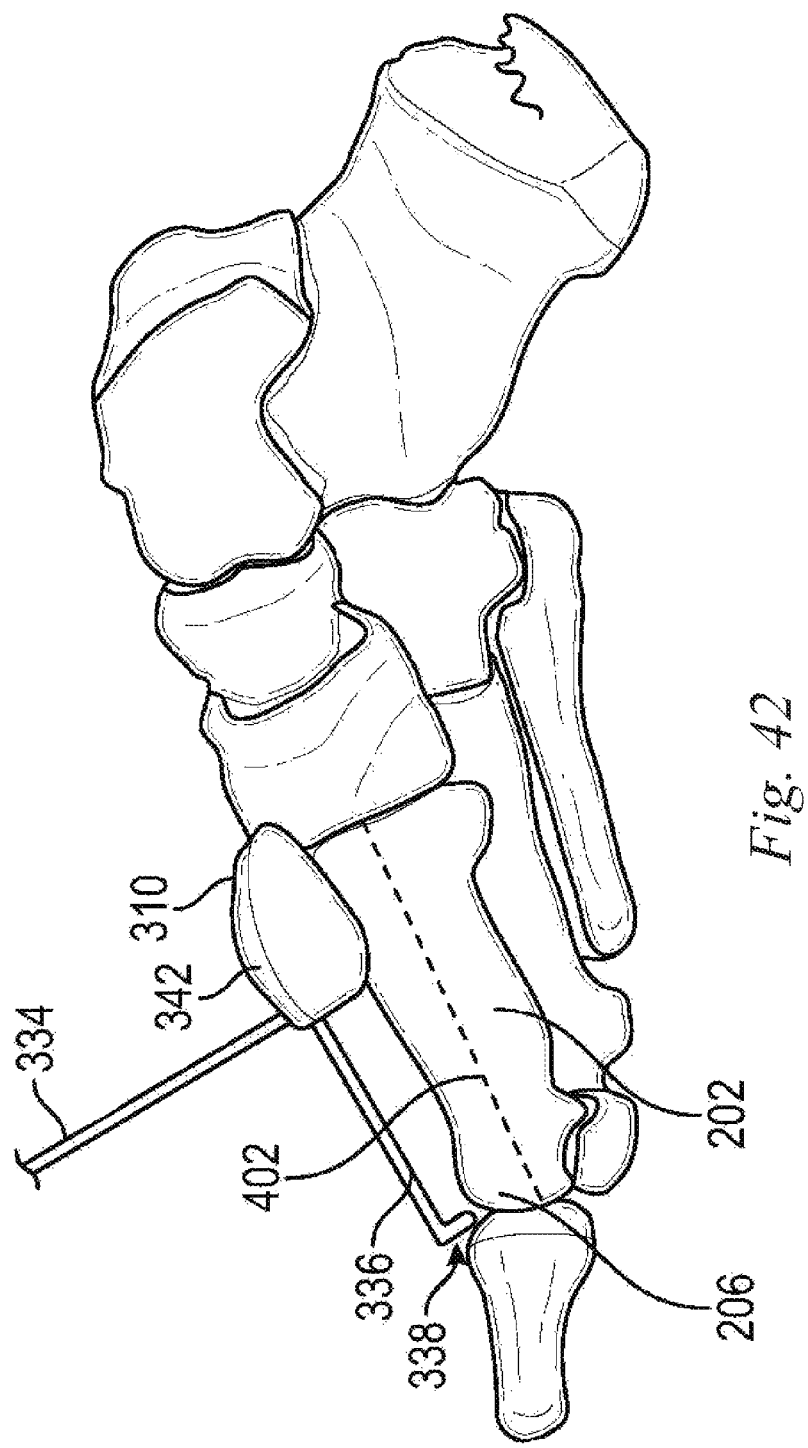
Figure 43:
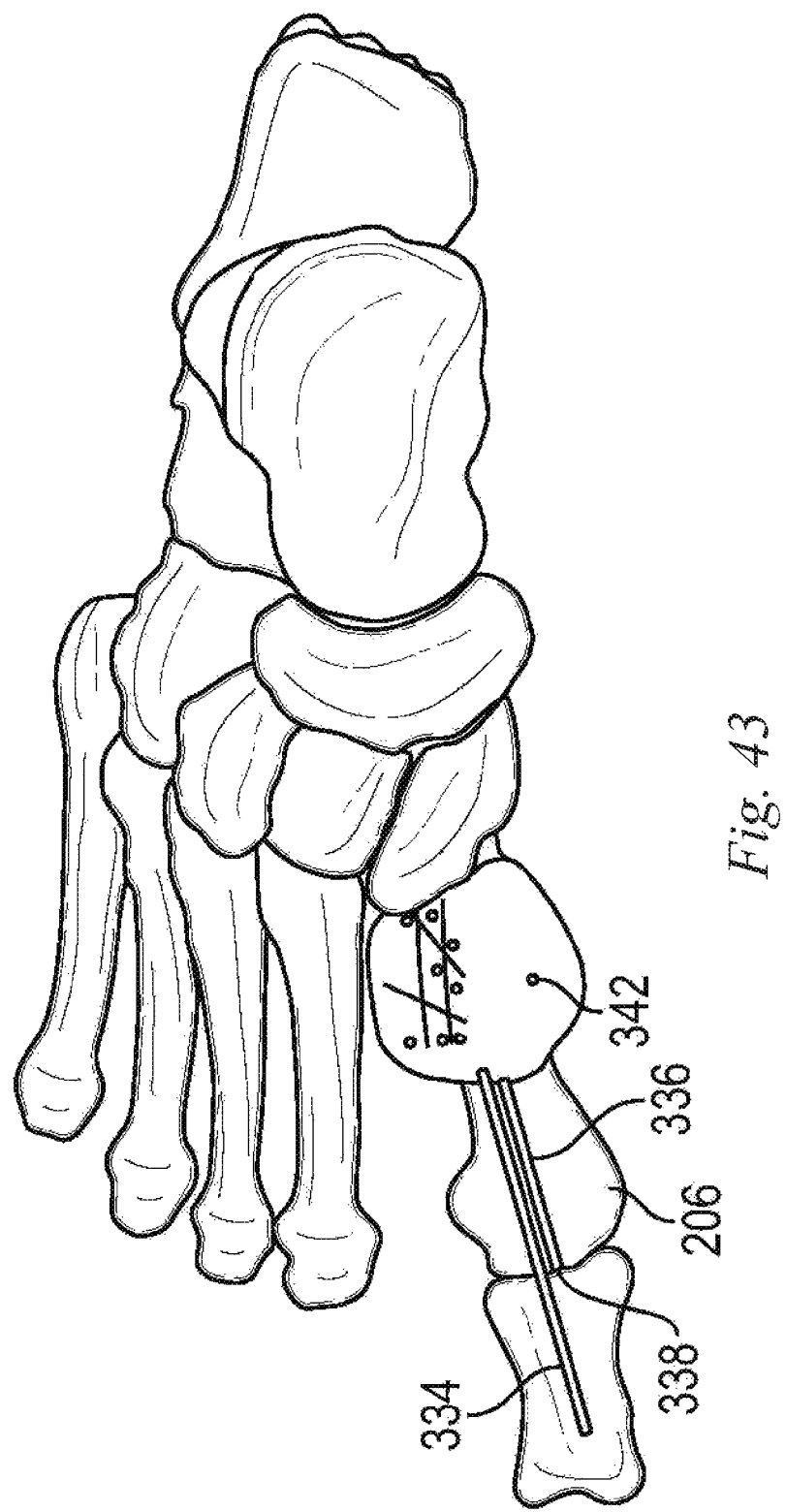

In FIGS. 42 and 43, the illustrative axis guide 310 of FIGS. 35-41 has been placed on the metatarsus 202. The dorsal alignment rod 334 is aligned with the local sagittal plane of the metatarsus 202. The distal alignment rod 336 is aligned parallel to the metatarsal anatomic axis 402. The optional pointer 338 may be aligned with e.g. the joint line of the MTP joint to position the axis guide 310 at a predetermined distance from the distal head 206. With the axis guide 310 at a predetermined distance from the distal head 206, angular changes in the position of the distal head 206 may optionally be expressed as displacements. For example, in the illustrative axis guide 310 of FIGS. 35-41, the change in dorsiflexion is indicated on the axis guide 310 as a plantar displacement of the metatarsal head. The dorsal alignment rod 334 may be driven into the metatarsus to temporarily fix the axis guide 310 in the aligned position.

Figure 44:
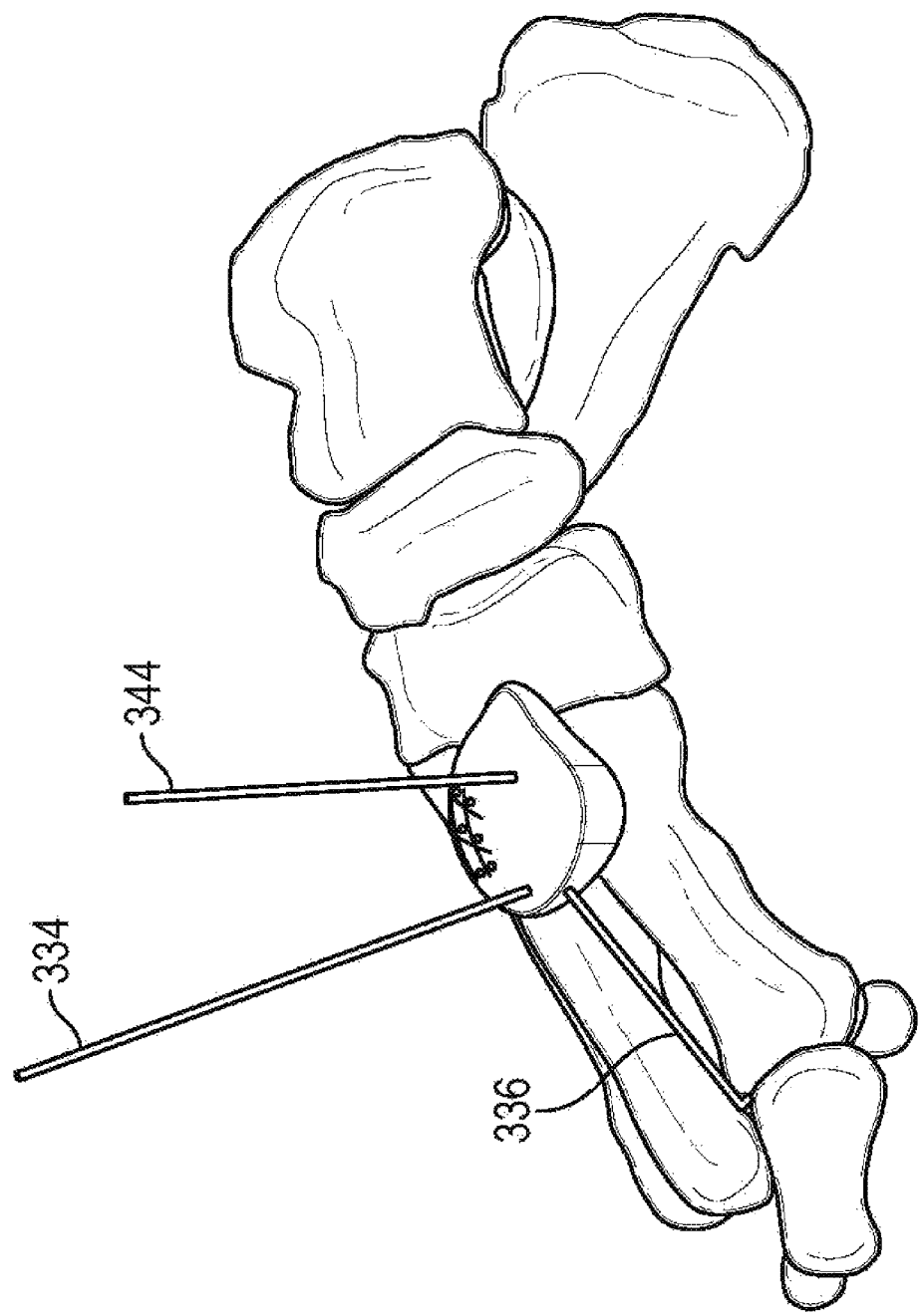

In FIG. 44, an additional pin 344 has been placed through the additional fixation hole 342 to further stabilize the axis guide 310.

Figure 45:
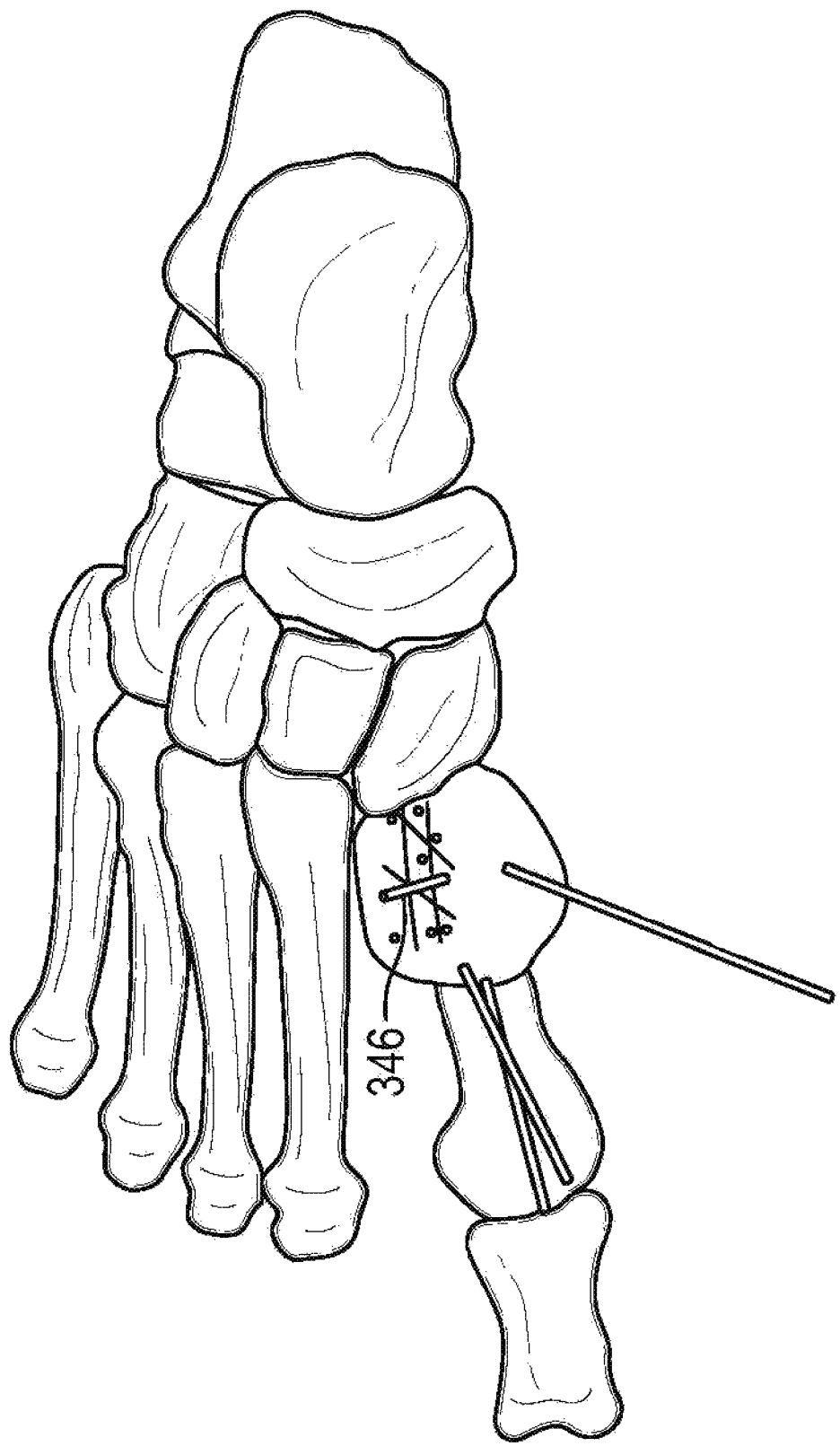

In FIG. 45, an axis pin 346 has been placed through the axis hole corresponding to a 15 degree change in IMA and a 5 degree change in pronation. The particular axis guide 310 also incorporates a 2.5 mm distal plantar displacement into each of the axis holes.

Figure 46:
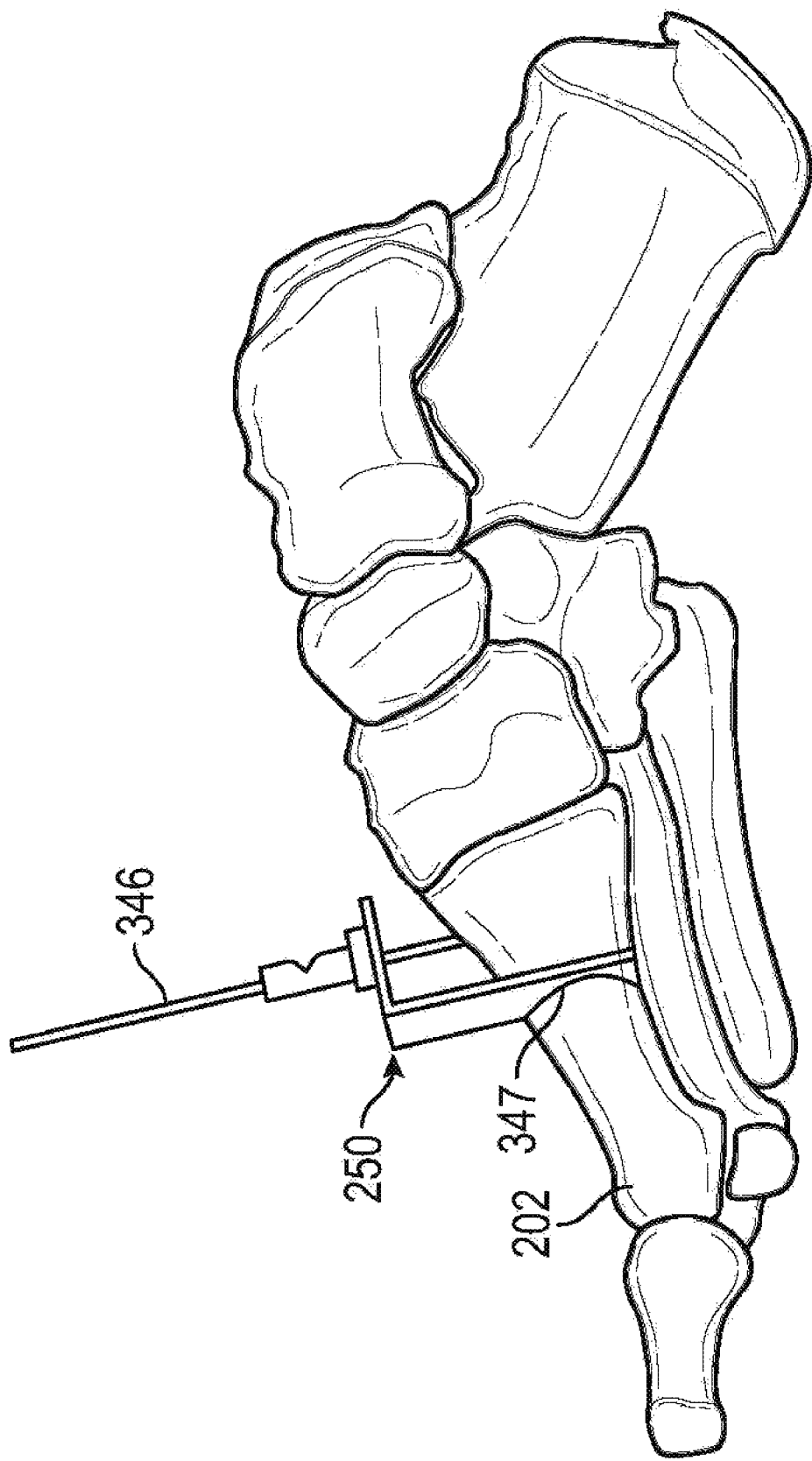

In FIG. 46, alignment rods 334 and 336, the fixation pin 344, and the axis guide 310 have been removed leaving just the axis pin 346 establishing the rotation axis for a 15 degree IMA, 5 degree pronation, and 2.5 mm distal plantar displacement corrective osteotomy. In the illustrative example of FIG. 46, the cannulated crescentic saw blade 250 has been placed over the axis pin 346 and rotated about the rotational axis pin 346 to produce a cylindrical cut 347 through the metatarsus 202. Alternatively, the cut block 270 may be placed over the rotational axis pin 346. The crescentic blade 250 may be guided on the cut block 270 alone, without engaging the pin 346, or the blade 250 may engage both the cut block 270 and the rotational axis pin 346. After the bone is cut, the distal portion is reduced to the desired IMA which will simultaneously change the pronation angle and plantar position of the distal bone portion. The bone portions may then be fixed with pins, screws, plates or other suitable fixation elements.

In FIG. 47, as an alternative to using the cannulated crescentic blade 250, the blade guide 280 has been placed over the rotational axis pin 346 and adjusted to align with a desired cut plane on the metatarsus 202. The set screw 291 is tightened to lock the blade guide 280 in place on the axis pin 346. A saw blade (not shown) is guided in the slot 294 to form a planar cut surface through the bone. After the bone is cut, the distal portion is reduced to the desired IMA which will simultaneously change the pronation angle and plantar position of the distal bone portion. The bone portions may then be fixed with pins, screws, plates or other suitable fixation elements.

Figure 50:
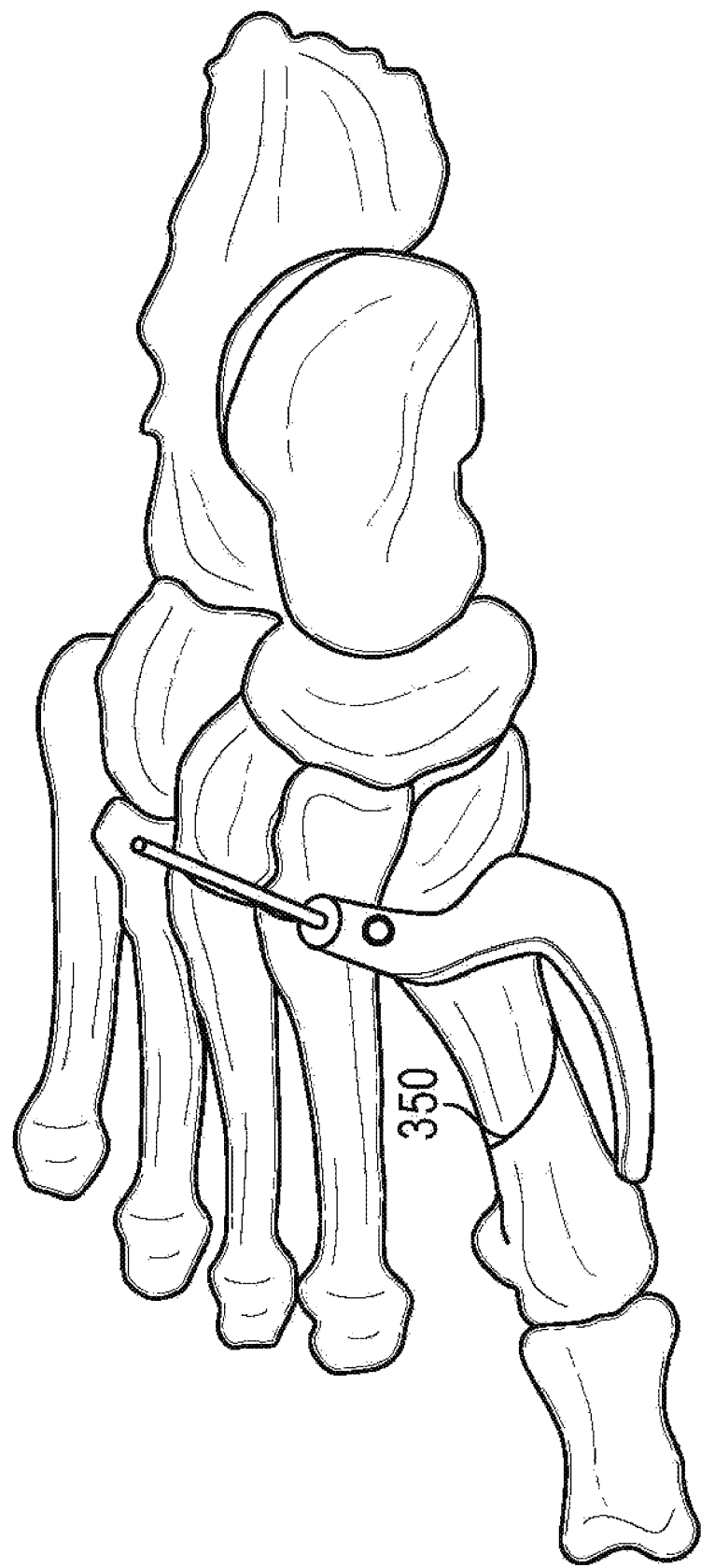
Figure 51:
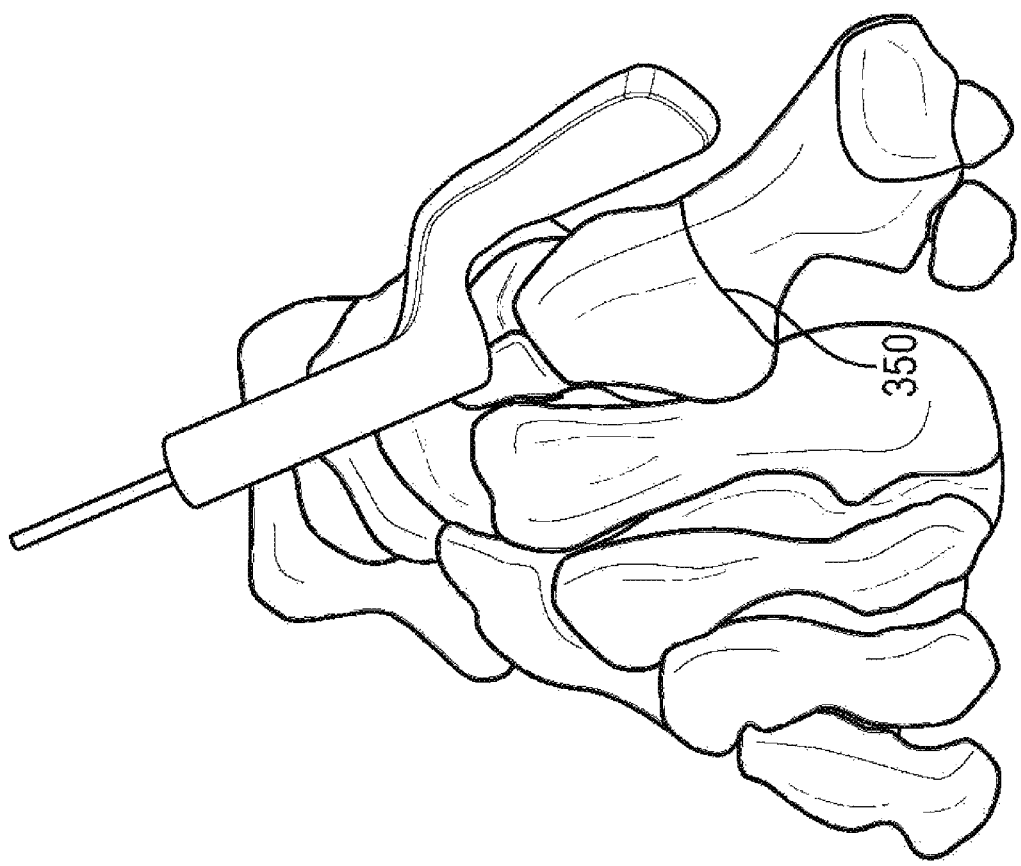

Referring to FIGS. 48 and 49, the rotational axis pin 346 may preferably be advanced partway into the bone as shown in FIG. 48 prior to cutting the bone so that the tip of the pin is dorsal to the slot 294. The bone may then be cut partially through, including under the rotational axis pin 346. The set screw 291 may be loosened and the rotational axis pin 346 driven plantar past the planar cut as shown in FIG. 49. The set screw 291 may be retightened and the remainder of the bone cut through. The bone cut 350 is shown in FIGS. 50 and 51. In this way, the rotational axis pin 346 captures the cut bone portions.

Figure 52:
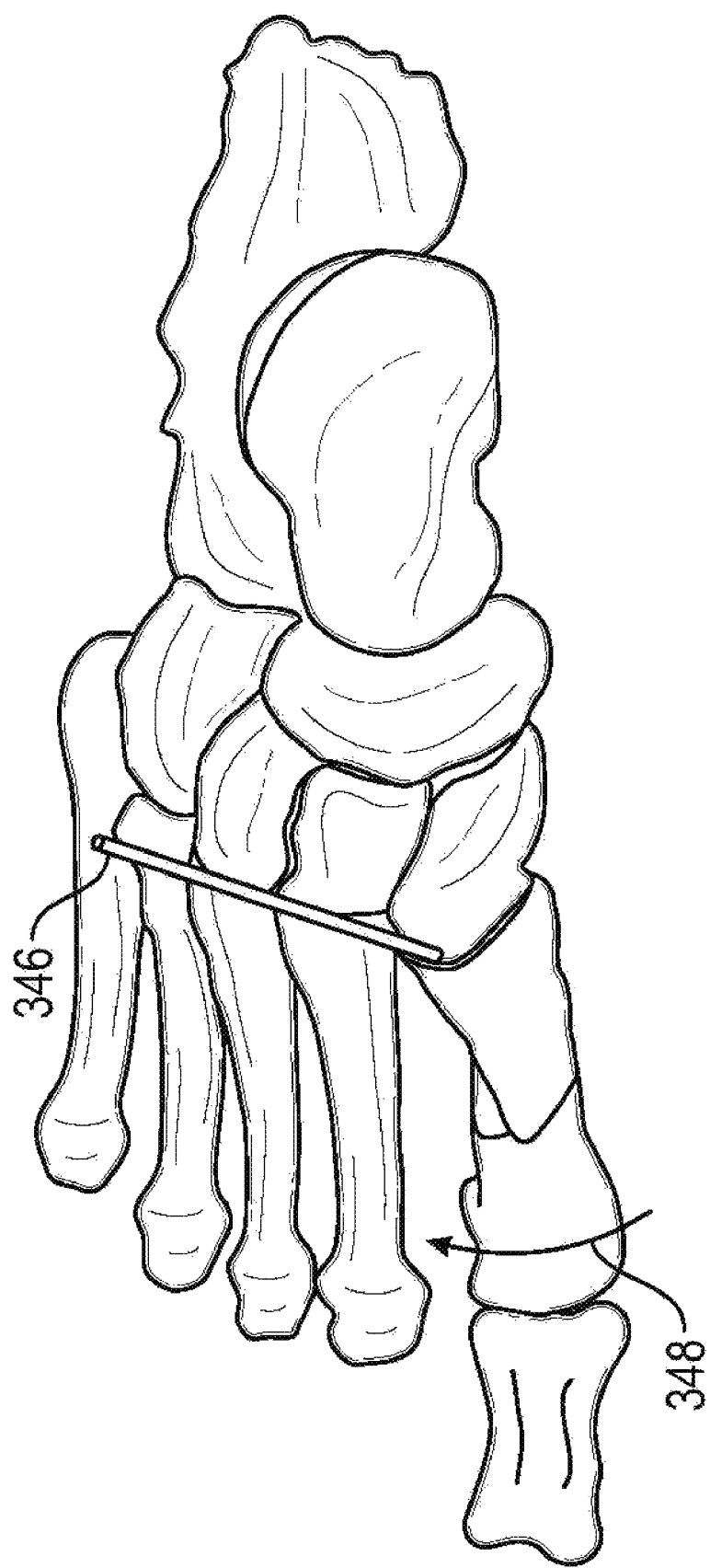
Figure 53:
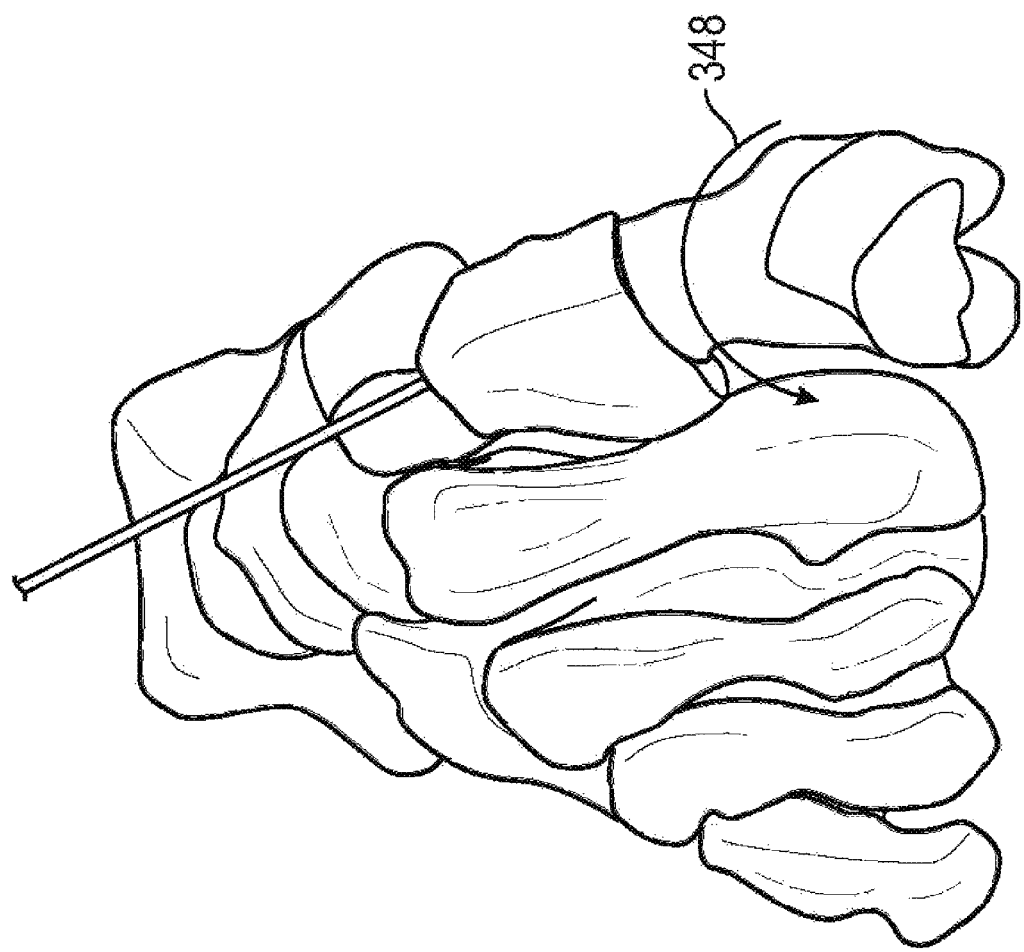
Figure 54:
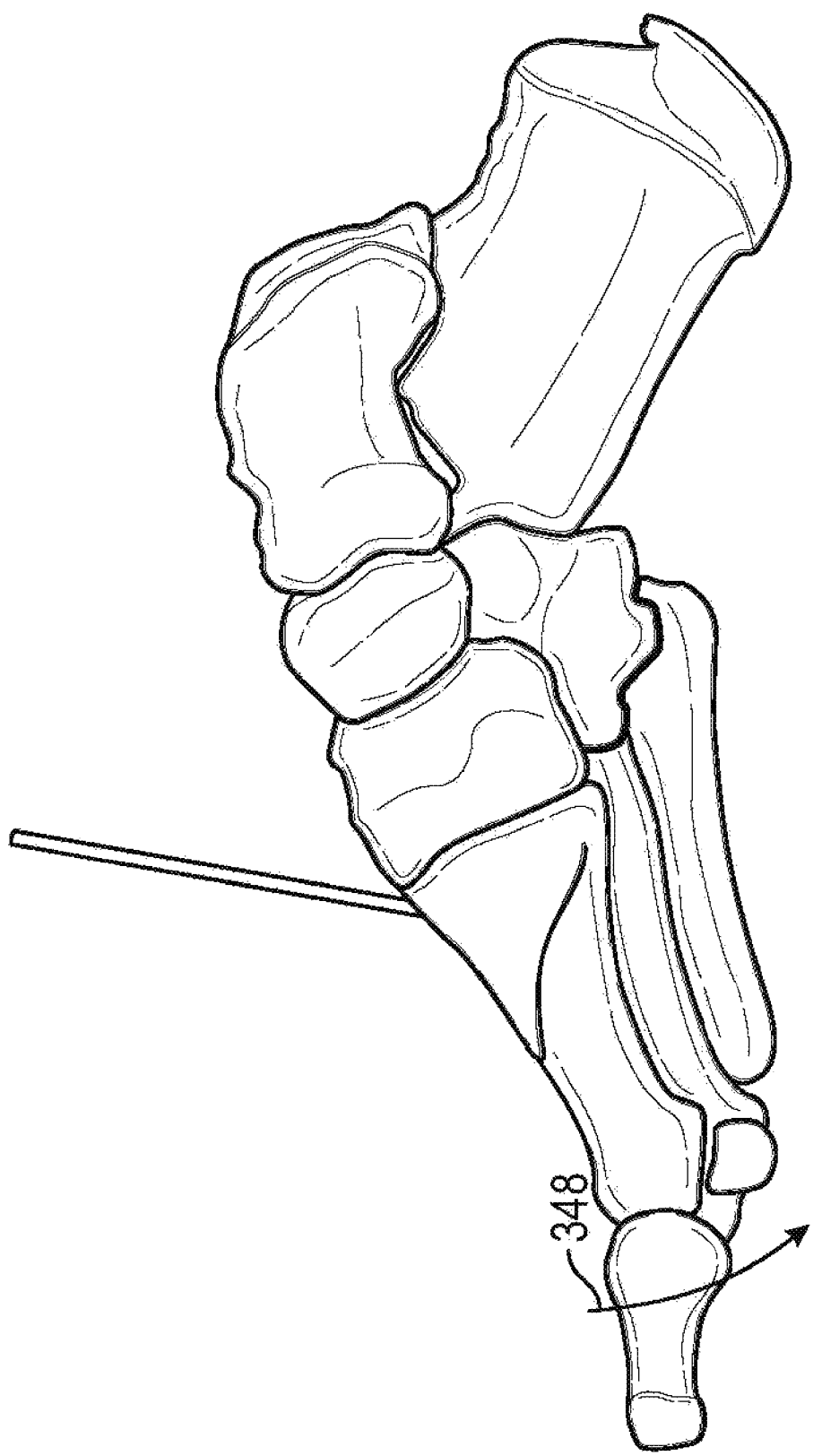
Figure 56:
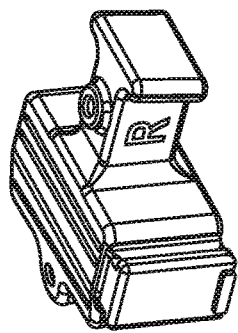
FIG. 56 is another isometric view of the cut guide of FIG. 55.
Figure 61:
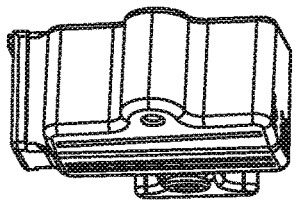
FIGS. 57-61 are orthographic views of the cut guide of FIG. 55.
Figure 57:
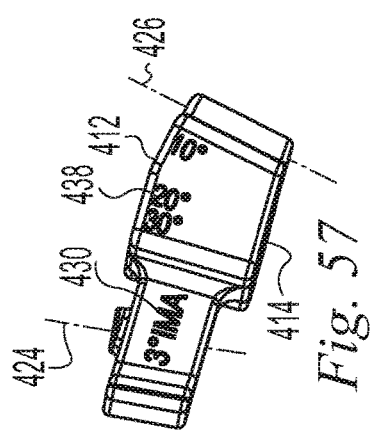
Figure 58:
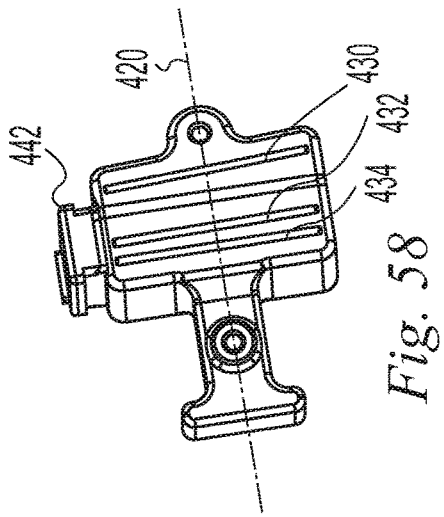
Figure 59:
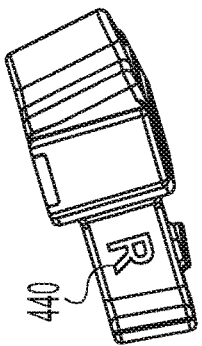

FIGS. 52-54 shows the bone with the blade guide 280 removed and the rotational axis pin 346 capturing the cut bone portions. The bone portions have been rotated as indicated by arrow 348 about the rotational axis pin to the desired IMA (FIG. 52) simultaneously changing the pronation angle (FIG. 53) and plantar position (FIG. 54) of the distal bone portion.

FIGS. 55-61 illustrate an alternative cut guide 400. The cut guide may be used to directly guide a cutter, such as a planar saw blade, to create a rotation plane between bone portions corresponding to a multi-planar correction as described relative to the examples above. The cut guide 400 includes a cutter guiding feature defining a rotation plane and includes reference features that are alignable with a bone to place the guide in a predetermined orientation relative to the bone. For sake of clarity, the cutter guiding surface is normal to a rotation axis determined as described above. However, in the illustrative example of FIGS. 55-61, the rotation axis is not discretely defined with a hole or pin but rather the corresponding plane is defined and referenced to the bony anatomy with the reference features.

In the illustrative example of FIGS. 55-61, the guide 400 includes a guide body 402 having a proximal end 404, a distal end 408 opposite the proximal end, a medial side 408, a lateral side 410 opposite the medial side, a top surface 412, and a bottom surface 414 opposite the top. The guide body 402 includes a fixation feature to temporarily secure the guide body 402 to a bone. The fixation features may include one or more roughened surface, spike, hole for receiving a pin or screw, strap, or other fixation feature known in the art. In the illustrative example of FIGS. 55-61, the fixation feature include holes 416, 418 extending through the guide body 402 from the top surface 412 to the bottom surface 414 and configured to receive a fixation member such as a pin or screw that extends though the guide body 402 and into the bone. Preferably the holes 416 and 418 are coplanar but not parallel. By being coplanar the hole axes define a reference plane that can be used to align the guide. By being non-parallel, smooth pins inserted through the holes and into an underlying bone will secure the guide body 402 to the bone and prevent it from lifting off of the bone. In the illustrative example of FIGS. 55-61, the holes 416, 418 define a plane including a guide body longitudinal axis 420 intersecting the hole axes 422, 424.

The guide body includes reference features for aligning the guide body with a metatarsus. In the illustrative example of FIGS. 55-61, the reference features include the bottom surface 414, the proximal end 404, and the longitudinal axis 420 defined by the holes 416, 418.

The guide body 402 includes a plurality of cutter guiding features, each corresponding to a different multi-planar correction. The cutter guiding features may be, for example, planar surfaces, slots, or other features known in the art for guiding a cutter to form a planar surface on a bone. In the illustrative example of FIGS. 55-61, the cutter guiding features are in the form of saw blade slots 430, 432, 434. Each slot 430, 432, 434 is aligned relative to the reference features so that when bottom surface 414 is resting on the bone, the longitudinal axis 420 is aligned parallel with the metatarsal axis, the hole axes 424, 426 are aligned within the sagittal plane, and the proximal end 404 is aligned with the MTC joint line, the slot will guide a saw blade to produce a rotation plane corresponding to a particular multi-planar correction. In the illustrative example of FIGS. 55-61, each slot is configured to produce 3 degrees of IMA correction and 10, 20, or 30 degrees of pronation correction. In addition, a slight amount of plantar displacement of the distal metatarsal head is included in each correction to compensate for shortening of the metatarsus due to the bone removed by the saw blade, i.e. the saw blade kerf. The amount of plantar displacement is an estimate based on an osteotomy-to-distal metatarsal head distance determined as the difference between the overall length of an average human first metatarsus and the distance from the MTC joint line to the osteotomy plane. In the illustrative example of FIGS. 55-61, the plantar displacement is designed to maintain the metatarsal head in the same plane it was in prior to the osteotomy to avoid changing the load balance between the five rays of the foot. Typical values of plantar displacement are in the range of 0.1 mm to 3 mm. In the illustrative example of FIGS. 55-61, the slots 430, 432, 434 define planes that are angled relative to one another in at least two rotational degrees of freedom.

Indicia 436, 438 printed on the guide body 402 indicate the IMA correction associated with all of the saw slots on the guide 400 and the different pronation correction associated with each of the saw slots. Additional indicia 440 printed on the guide body 402 indicates that the guide 400 is configured for a right foot.

A handle may be provided to aid in manipulating the guide 400. In the illustrative example of FIGS. 55-61, a handle interface 442 is formed on the medial side to engage a modular, removable handle (not shown). The handle interface may include a slot, tab, dovetail, or other feature as is known in the art for coupling to a modular handle.

Figure 55:
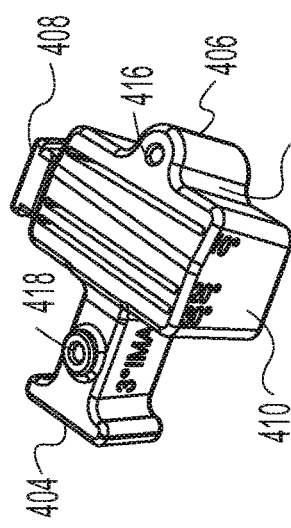
FIG. 55 is an isometric view of a cut guide according to the present invention.
Figure 60:
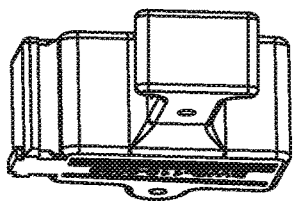
Figure 62:
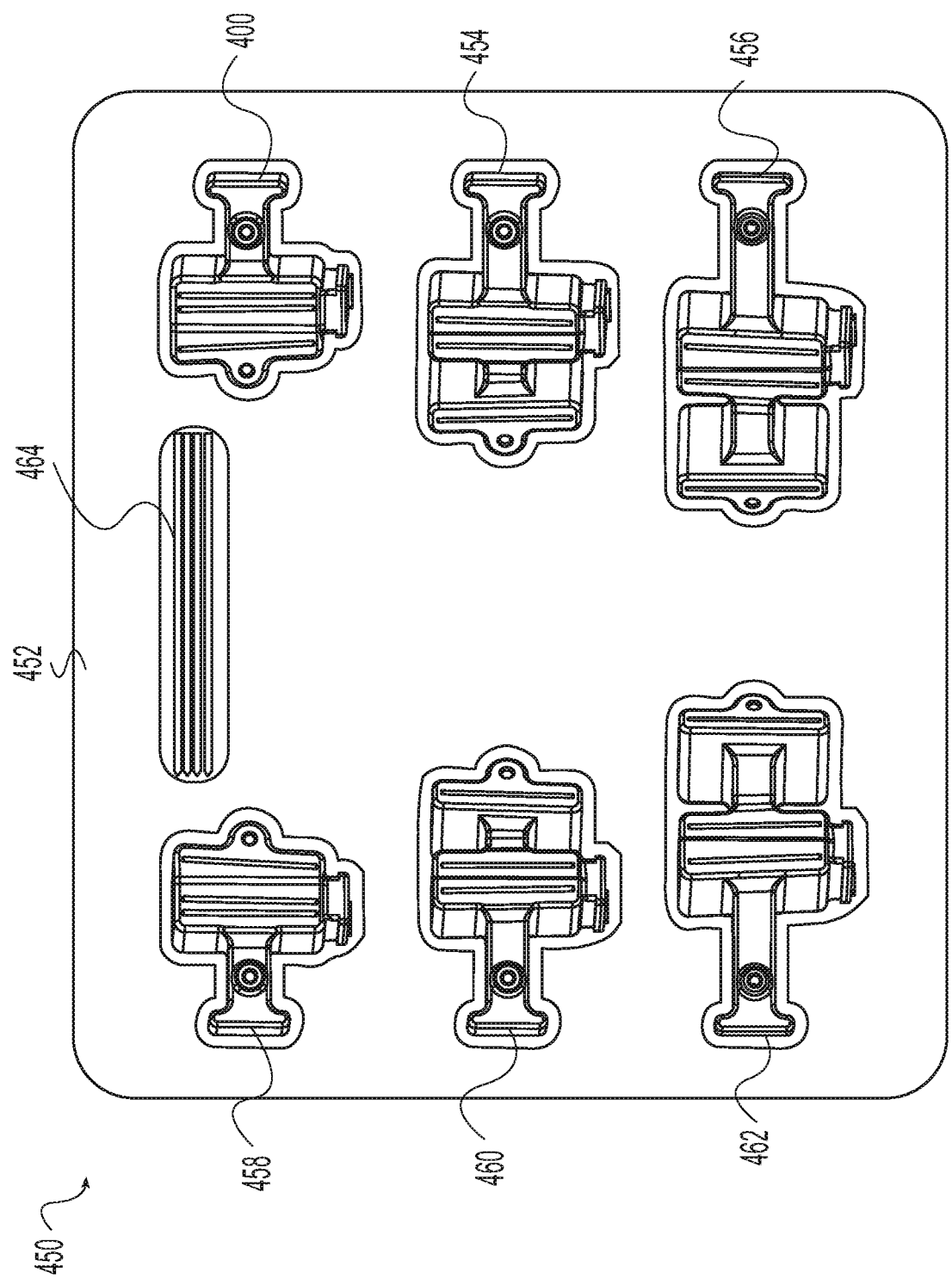
FIG. 62 is a top plan, or dorsal, view of a set of cut guides including the cut guide of FIG. 55 and additional similar guides having varying sizes and orientation.

FIG. 62 depicts an exemplary kit 450 having a tray 452 for housing the guide 400 of FIG. 55 along with additional guides offering a variety of configurations. In the illustrative example of FIG. 62, a plurality of guides 400, 454, 456 configured for a right foot is provided on one side of the tray 452 and a plurality of guides 458, 460, 462 configured for a left foot is provided on another side of the tray. In the illustrative example of FIGS. 55-61, each guide provides for either 3, 6, or 9 degrees of IMA correction and the choice of 10, 20, or 30 degrees of pronation correction. All of the guides provide a fixed additional plantar displacement. The kit allows a surgeon to select a guide corresponding to a left or right foot and having a desired amount of IMA correction. After selecting the appropriate guide, the surgeon may then select the amount of pronation correction by choosing the corresponding saw slot. The tray may include other items useful in the osteotomy procedure such as fixation pins 464.

Figure 63:
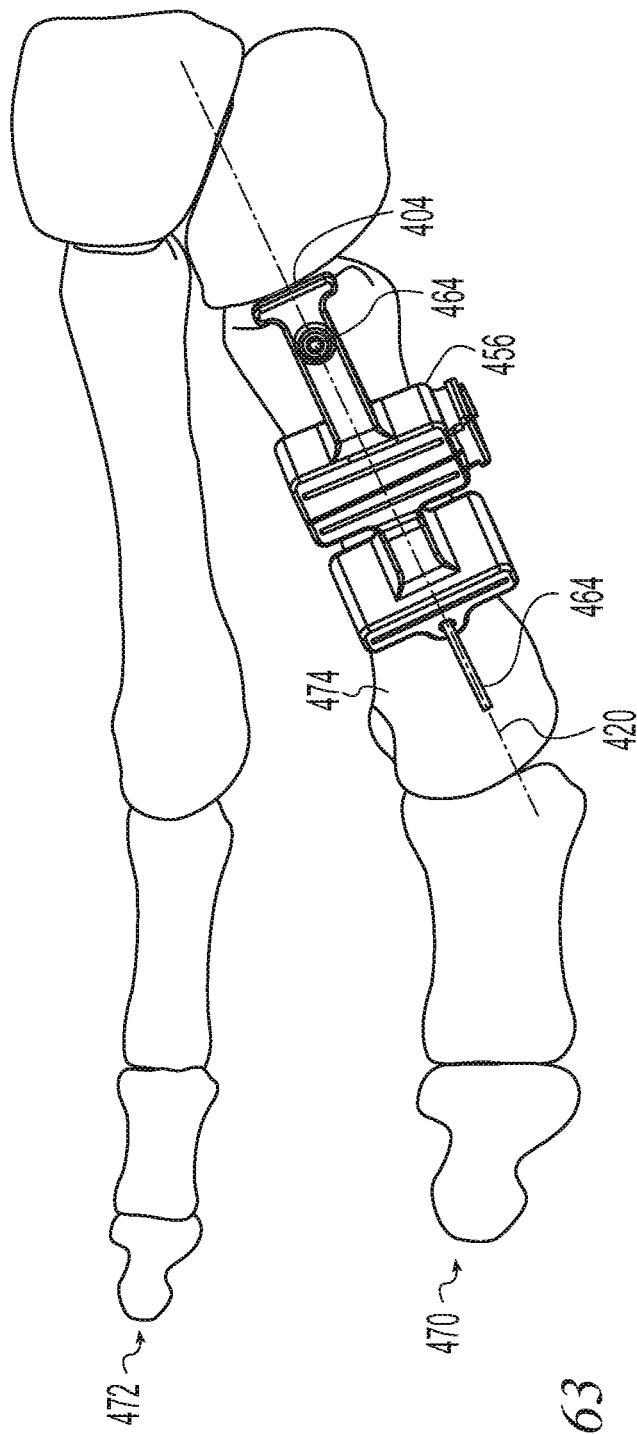
FIGS. 63-65 illustrate a method of performing an osteotomy on a bone according to the present invention utilizing one of the cut guides of FIG. 62.
Figure 64:
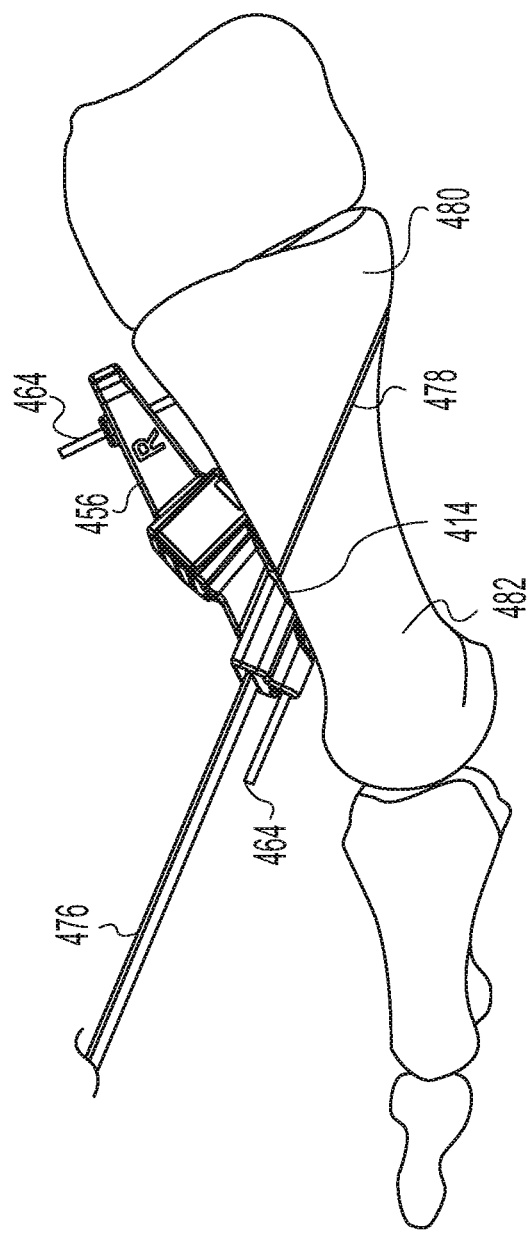
Figure 65:
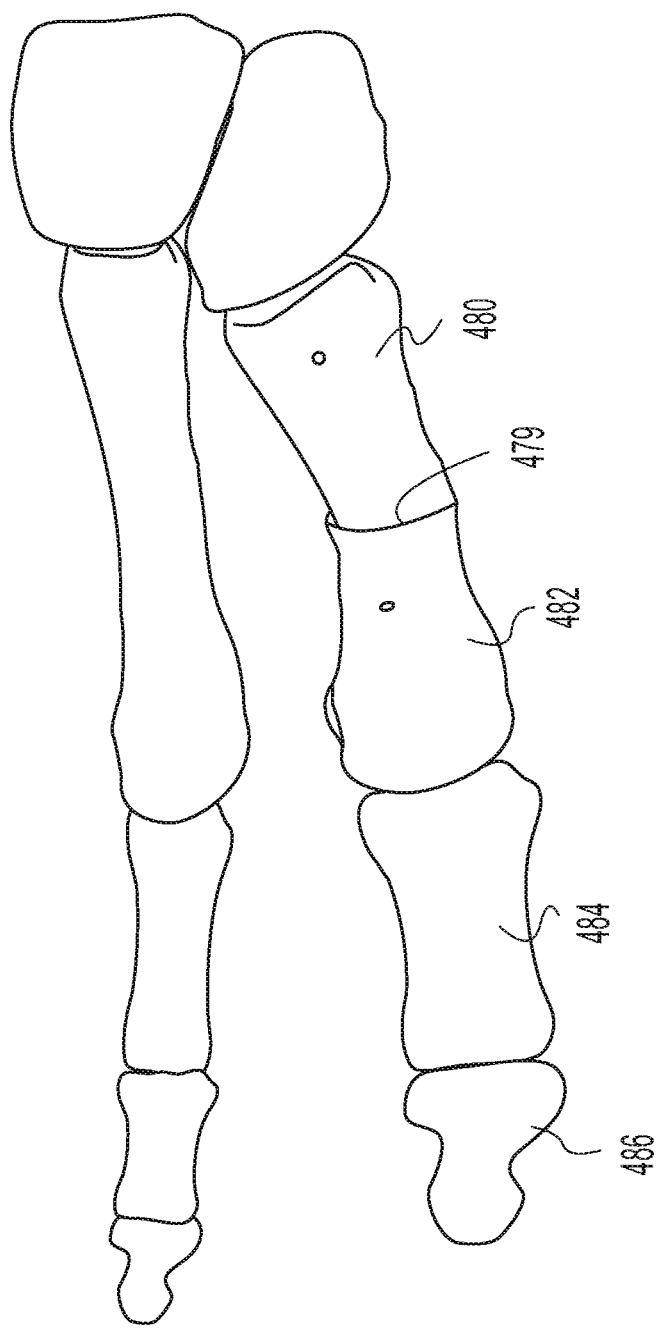

FIGS. 63-65 illustrate an osteotomy procedure using the kit 450. FIG. 63 is a dorsal view of the first and second rays 470, 472 of a right foot having an IMA of approximately 19 degrees. A guide 456 is selected from the kit 450 corresponding to a 9 degree IMA correction. The guide 456 is mounted on the metatarsus 474 with the bottom of the guide 456 resting on the longitudinal axis 420 of the guide, the longitudinal axis 420 parallel to the metatarsal longitudinal axis, the plane containing the fixation hole axes 426, 424 aligned parallel to the sagittal plane, and the proximal end aligned with the MTC joint. In the illustrative example of FIGS. 63-65, the surgeon selects the saw slot corresponding to a 10 degree pronation correction and uses it to guide a saw blade 476 to form a cut 478 defining a rotation plane 479 between proximal and distal portions 480, 482 of the metatarsus.

In FIG. 65, the distal portion of the metatarsus along with the phalanges 484, 486 have been rotated within the plane 479 defined by the cut 478 to reduce the IMA by 9 degrees as well as correct the pronation by 10 degrees and produce a compensating plantar displacement of the metatarsal head. If desired, the surgeon may fine tune the position of the distal portion of the first ray by sliding the cut surfaces in addition to rotating them. The osteotomy may be fixed using pins, screws, plates, or other devices and methods as is known in the art.

Various illustrative examples of devices and methods of producing a multi-planar osteotomy on a bone have been provided. Examples of guides have been provided that can be used to define a rotation axis and/or corresponding rotation plane in three rotational degrees of freedom relative to a bone to perform a tri-planar rotational osteotomy. While such a guide may be used to perform a tri-planar rotational osteotomy on any bone, it has been illustrated for example to produce a tri-planar rotational osteotomy on a first metatarsus of a human foot to correct angular alignment of the first ray of the foot. The illustrative examples are particularly useful to a surgeon inasmuch as they provide the surgeon with the ability to intraoperatively select at least one of the correction angles. For example, an exemplary guide has been disclosed that allows the surgeon to vary the value of one of the three angular degrees of freedom simply by choosing one of a plurality of guiding features such as a hole defining a rotation axis or a surface or slot defining a rotation plane. An exemplary guide has been disclosed that allows the surgeon to vary the value of two of the three angular degrees of freedom by selecting one of a plurality of guiding features arranged in a matrix. Sets of guides have been disclosed that allow the surgeon to intraoperatively vary a third angular degree of freedom. It has been shown that the angular degrees of freedom may be stated in terms of rotational degrees or as displacements if additional information is provided regarding the size and shape of the bone and the location of the osteotomy. Examples have been disclosed in which the angular degrees of freedom may be related to a metatarsus of a foot so that they correspond to, for example, IMA, pronation, and plantar flexion. Guides have been disclosed that may be configured to allow user selectability of any one of IMA, pronation, and plantar flexion. Guides have been disclosed that may be configured to allow user selectability of any two of IMA, pronation, and plantar flexion. Guides have been disclosed as sets of guides that may be configured to allow user selectability of IMA, pronation, and plantar flexion. Guides have been disclosed having a plurality of cutter guiding features differing in the amount of angular correction. It is within the scope of the invention to provide a single cutter guiding feature with an adjustable position to permit varying the value of one or more angular corrections. It will be understood that substitutions among the various examples and variations are within the scope of the invention. For example, more or fewer options with regard to correction angles may be provided, alternative fixation of the guide to the bone may be incorporated, and different corrections may be coupled on a particular guide. For example, a particular guide may have a fixed pronation correction and variable IMA correction or a particular guide or set of guides may have variable plantar displacement. Many combinations are possible and the present inventors have demonstrated multiple, but not a comprehensive listing of, examples illustrating some of the possible combinations of features within the scope of the invention.

What is claimed is:

1. An osteotomy system operable to guide the formation of a tri-planar rotational osteotomy between a proximal portion of a metatarsal bone and a distal portion of the metatarsal bone, the tri-planar rotational osteotomy being operable to establish an orientation between the proximal and distal portions of the metatarsal bone incorporating coupled changes in at least two of the intermetatarsal angle, pronation, and plantar flexion of the distal portion of the metatarsal bone, the osteotomy system comprising:
   a set of cutter guides, each member of the set of cutter guides comprising:
      reference features operable to align the cutter guide with the metatarsal bone in a predetermined position; and
      one or more cutter guiding features each defining an osteotomy plane or rotation axis relative to the metatarsal bone, the osteotomy plane or rotation axis corresponding to fixed changes in at least two of intermetatarsal angle, pronation, and plantar flexion of the distal portion of the metatarsal bone, at least one of the change in intermetatarsal angle, pronation, and plantar flexion being user selectable among a plurality of values at the time of surgery,
      wherein each member of the set of cutter guides has a fixed value for at least one of the change in intermetatarsal angle, pronation, and plantar flexion that is different from that of another member of the set of cutter guides; and
   a cutter operable to be guided by one of the one or more cutter guiding features to cut the metatarsal bone to mobilize the proximal portion of the metatarsal bone and the distal portion of the metatarsal bone relative to one another and produce cut surfaces on which the distal portion of the metatarsal bone and the proximal portion of the metatarsal bone are relatively rotatable.

2. The osteotomy system of claim 1 wherein the one or more cutter guiding features comprises a plurality of cutter guiding features in which each of the plurality of cutter guiding features defines an osteotomy plane or rotation axis differing from that of another cutter guiding feature in at least one of the amount of change in intermetatarsal angle, pronation, and plantar flexion.

3. The osteotomy system of claim 1 wherein at least two of the change in intermetatarsal angle, pronation, and plantar flexion are user selectable among a plurality of values at the time of surgery.

4. The osteotomy system of claim 1 wherein the one or more cutter guiding features comprises a plurality of saw blade guiding surfaces.

5. The osteotomy system of claim 4 wherein the plurality of saw blade guiding surfaces comprises a plurality of saw slots.

6. The osteotomy system of claim 5 wherein each member of the set of cutter guides has a plurality of slots in which each slot within that particular guide corresponds to a different osteotomy plane producing a same change in intermetatarsal angle but a different change in pronation, the change in intermetatarsal angle produced by the slots of each guide differing from the change in intermetatarsal angle produced by the slots of another guide.

7. The osteotomy system of claim 6 wherein each slot in the plurality of slots of each guide produces a change in plantar displacement of the distal end of the metatarsal bone that is the same as each other slot.

8. The osteotomy system of claim 7 wherein the change in plantar displacement of the distal end of the metatarsal bone is the same for all guides in the set of guides.

9. The osteotomy system of claim 5 wherein each member of the set of cutter guides has a plurality of slots in which each slot within that particular guide corresponds to a different osteotomy plane producing a same change in pronation but a different change in intermetatarsal angle, the change in pronation produced by the slots of each guide differing from the change in pronation produced by the slots of another guide.

10. An osteotomy system operable to guide the formation of a tri-planar rotational osteotomy between a proximal portion of a metatarsal bone and a distal portion of the metatarsal bone, the osteotomy system comprising:
at least one cutter guide comprising:
reference features operable to align the cutter guide with the metatarsal bone in a predetermined position;
at least two cutter guiding features each defining an osteotomy plane or rotation axis relative to the metatarsal bone, the osteotomy plane or rotation axis corresponding to fixed changes in at least two of intermetatarsal angle, pronation, and plantar flexion of the distal portion of the metatarsal bone, the at least two cutter guiding features defining osteotomy planes that are angled relative to one another in at least two rotational degrees of freedom; and
indicia printed on a guide body of the at least one cutter guide indicating that the at least one cutter guide is configured for a right foot or for a left foot.

11. The osteotomy system of claim 10 further comprising a cutter operable to be guided by one of the at least two cutter guiding features to cut the metatarsal bone to mobilize the proximal portion of the metatarsal bone and the distal portion of the metatarsal bone relative to one another and produce cut surfaces on which the distal portion of the metatarsal bone and the proximal portion of the metatarsal bone are relatively rotatable.

12. The osteotomy system of claim 10 further comprising one or more fixation pins suitable for fixing the at least one cutter guide to the metatarsal bone.

13. The osteotomy system of claim 10 wherein the at least one cutter guide comprises a plurality of cutter guides, the plurality of cutter guides comprising at least one cutter guide configured for a right foot and at least one cutter guide configured for a left foot.

14. The osteotomy system of claim 13 further comprising a tray housing the plurality of cutter guides.

15. The osteotomy system of claim 14 wherein the at least one cutter guide configured for a right foot is housed within a right side of the tray and wherein the at least one cutter guide configured for a left foot is housed within a left side of the tray.

16. The osteotomy system of claim 13 wherein the plurality of cutter guides comprises a plurality of cutter guides configured for a right foot and a plurality of cutter guides configured for a left foot, each of the plurality of cutter guides configured for a right foot corresponding to a different change of intermetatarsal angle relative to at least one other cutter guide of the plurality of cutter guides configured for a right foot, each of the plurality of cutter guides configured for a left foot corresponding to a different change of intermetatarsal angle relative to at least one other cutter guide of the plurality of cutter guides configured for a left foot.

17. The osteotomy system of claim 10 wherein each of the at least two cutter guiding features comprises a slot.

18. The osteotomy system of claim 17 wherein each of the slots are aligned parallel to the reference features.

* * * * *